United States Patent
Patterson, III et al.

(10) Patent No.: US 11,890,102 B2
(45) Date of Patent: Feb. 6, 2024

(54) SYSTEMS AND METHODS FOR PROVIDING AN ALERT INDICATING BATTERY REMOVAL FROM A WEARABLE MEDICAL DEVICE

(71) Applicant: ZOLL Medical Corporation, Chelmsford, MA (US)

(72) Inventors: James A. Patterson, III, Claridge, PA (US); Nathan J. Berry Ann, Cranberry Township, PA (US); Sean M. Nickel, Monroeville, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 299 days.

(21) Appl. No.: 17/060,398

(22) Filed: Oct. 1, 2020

(65) Prior Publication Data

US 2021/0100467 A1    Apr. 8, 2021

Related U.S. Application Data

(60) Provisional application No. 62/910,673, filed on Oct. 4, 2019.

(51) Int. Cl.
*A61B 5/349* (2021.01)
*A61B 5/25* (2021.01)
*A61B 5/00* (2006.01)

(52) U.S. Cl.
CPC ............... *A61B 5/349* (2021.01); *A61B 5/25* (2021.01); *A61B 5/4836* (2013.01);
(Continued)

(58) Field of Classification Search
CPC .................... A61B 5/349; A61B 5/25
(Continued)

(56) References Cited

U.S. PATENT DOCUMENTS 5,574,436 A    11/1996 Sisselman et al.
5,764,034 A    6/1998 Bowman et al.
(Continued)

FOREIGN PATENT DOCUMENTS

EP        3109927 A1    12/2016
WO    WO-2018004685 A1 *  1/2018  ............. G04G 17/04

OTHER PUBLICATIONS

Extended European Search Report for Application No. 20275156.6 dated Feb. 22, 2021, 8 pages.

*Primary Examiner* — Nicole F Lavert
(74) *Attorney, Agent, or Firm* — ZOLL Medical Corporation

(57) ABSTRACT

An externally worn cardiac monitoring and/or treatment system with battery detachment detection is provided. The system includes detachment circuitry and audible and/or vibrational alarm circuitry operably coupled to the detachment circuitry. The detachment circuitry is configured to detect whether the rechargeable battery is detached from the battery-powered externally worn cardiac device by monitoring a connection established between the rechargeable battery and the at least one processor and output a battery status signal indicating whether the rechargeable battery is detached from the battery-powered externally worn cardiac device. The audible and/or vibrational alarm circuitry is configured to receive the battery status signal and output an audible alert in a predetermined frequency range and/or a tactile alert if the rechargeable battery is detached.

15 Claims, 23 Drawing Sheets

(52) U.S. Cl.
CPC ............ *A61B 5/7405* (2013.01); *A61B 5/746* (2013.01); *A61B 5/7455* (2013.01); *A61B 2560/0214* (2013.01)

(58) Field of Classification Search
USPC ........................................................ 600/515
See application file for complete search history.

(56) References Cited

U.S. PATENT DOCUMENTS

| | | |
|---|---|---|
| 2008/0243079 A1 | 10/2008 | Wooley et al. |
| 2017/0003356 A1 | 1/2017 | Kaib et al. |
| 2017/0199797 A1* | 7/2017 | Hresko .................. G16H 10/60 |
| 2019/0192870 A1 | 6/2019 | Zaidi et al. |
| 2019/0252891 A1 | 8/2019 | Ploeg et al. |
| 2020/0101306 A1* | 4/2020 | Roberto ............. A61N 1/36135 |

* cited by examiner

SYSTEMS AND METHODS FOR PROVIDING AN ALERT INDICATING BATTERY REMOVAL FROM A WEARABLE MEDICAL DEVICE

RELATED APPLICATION

This application claims priority under 35 U.S.C. § 119 (e) to U.S. Provisional Application Ser. No. 62/910,673, titled "SYSTEMS AND METHODS FOR PROVIDING AN ALERT INDICATING BATTERY REMOVAL FROM A WEARABLE MEDICAL DEVICE," filed Oct. 4, 2019, which is hereby incorporated herein by reference in its entirety.

BACKGROUND

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient is generally instructed to keep a battery in the device at all times and one battery on the charger at all times. Thus, as one battery is being depleted by the device, the second battery is being charged. By following these instructions, when a battery swap is required, the second battery is charged and ready to power the wearable device. Upon swapping, the battery removed from the wearable device is inserted into the charger, and the process is repeated.

SUMMARY

In an example, an externally worn cardiac monitoring and/or treatment system with battery detachment detection is provided. The system includes a battery-powered externally worn cardiac device and a rechargeable battery. The battery-powered externally worn cardiac device includes a housing and at least one processor disposed in the housing and being configured to process one or more ECG signals of a patient wearing the battery-powered externally worn cardiac device and determine at least one arrhythmia based on the processed ECG signal. The rechargeable battery is detachably disposed within the housing of the battery-powered externally worn cardiac device and removably coupled to the at least one processor. The rechargeable battery includes at least one battery cell, detachment circuitry, and audible and/or vibrational alarm circuitry operably coupled to the detachment circuitry. The detachment circuitry is configured to detect whether the rechargeable battery is detached from the battery-powered externally worn cardiac device by monitoring a connection established between the rechargeable battery and the at least one processor and output a battery status signal indicating whether the rechargeable battery is detached from the battery-powered externally worn cardiac device. The audible and/or vibrational alarm circuitry is configured to receive the battery status signal and output an audible alert in a predetermined frequency range and/or a tactile alert if the rechargeable battery is detached.

Implementations of the externally worn cardiac monitoring and/or treatment system with battery detachment detection can include one or more of the following features.

In the system the detachment circuitry can be further configured to determine whether the rechargeable battery is inserted into a battery charger by monitoring for a recharging current going from the battery charger to the at least one battery cell and output an updated battery status signal indicating whether the rechargeable battery is inserted into a battery charger. In some examples of the system, the audible and/or vibrational alarm circuitry can be further configured to determine whether the rechargeable battery is inserted into a battery charger based upon the updated battery status signal and stop the output of the audible alert in a predetermined frequency range and/or the tactile alert if the rechargeable battery is inserted into a battery charger.

In the system, the audible and/or vibrational alarm circuitry can include at least one audio output device. In some examples of the system, the at least one audio output device can be adjustable to alter the predetermined frequency range of the audible alert. In some additional examples of the system, the at least one audio output device can be adjustable via a control provided during initial patient fitting of the battery-powered externally worn cardiac device. In some additional examples of the system, the at least one processor can be configured to adjust the predetermined frequency range based upon patient response to a hearing test administered by the battery-powered externally worn cardiac device during initial patient fitting of the battery-powered externally worn cardiac device. In some examples of the system, the battery-powered externally worn cardiac device can further include a user interface configured to adjust the at least one audio output device. In some additional examples of the system, the user interface can include a mechanical interface configured to physically manipulate at least one component of the audible and/or vibrational alarm circuitry to adjust the at least one audio output device. In some additional examples of the system, the user interface can include a display configured to receive one or more inputs from a user of the battery-powered externally worn cardiac device to adjust the at least one audio output device.

In the system, the audible and/or vibrational alarm circuitry can include at least one output device operably coupled to and receiving power from the at least one battery cell, the at least one output device being configured to output the audible alert in a predetermined frequency range and/or the tactile alert.

In the system, the detachment circuitry can include a detachment processor configured to detect whether the rechargeable battery is detached from the battery-powered externally worn cardiac device and output the battery status signal.

In the system, the battery-powered externally worn cardiac device can further include a plurality of sensing electrode configured to be coupled externally to a patient and to detect the one or more ECG signals of the patient wearing the battery-powered externally worn cardiac device.

In the system, the battery-powered externally worn cardiac device can further include at least one therapy electrode configured to deliver one or more therapeutic shocks to a patient wearing the battery-powered externally worn cardiac device. In some examples of the system, the rechargeable battery can be configured to provide power to the at least one therapy electrode to deliver the one or more therapeutic shocks to the patient wearing the battery-powered externally worn cardiac device. In some additional examples of the system, the one or more therapeutic shocks can include defibrillation shocks.

In another example, a battery-powered externally worn cardiac device with battery detachment detection is provided. The battery-powered externally worn cardiac device includes a housing, at least one processor disposed in the housing, and a rechargeable battery detachably disposed within the housing and removably coupled to the at least one processor. The at least one processor is configured to process one or more ECG signals of a patient wearing the battery-powered externally worn cardiac device and determine at least one arrhythmia based on the processed ECG signal. The rechargeable battery includes at least one battery cell, detachment circuitry, and audible and/or vibrational alarm circuitry operably coupled to the detachment circuitry. The detachment circuitry is configured to monitor for at least one signal indicating whether the rechargeable battery is detached from the battery-powered externally worn cardiac device, detect whether the rechargeable battery is detached in response to monitoring the at least one signal, and output a battery status signal indicating whether the rechargeable battery is detached from the battery-powered externally worn cardiac device. The audible and/or vibrational alarm circuitry is configured to receive the battery status signal and output an audible alert in a predetermined frequency range and/or a tactile alert if the rechargeable battery is detached.

Implementations of the battery-powered externally worn cardiac device with battery detachment detection can include one or more of the following features.

In the device, the detachment circuitry can be further configured to determine whether the rechargeable battery is inserted into a battery charger by monitoring for a recharging current going from the battery charger to the at least one battery cell and output an updated battery status signal indicating whether the rechargeable battery is inserted into a battery charger. In some examples of the device, the audible and/or vibrational alarm circuitry can be further configured to determine whether the rechargeable battery is inserted into a battery charger based upon the updated battery status signal and stop the output of the audible alert in a predetermined frequency range and/or the tactile alert if the rechargeable battery is inserted into a battery charger.

In the device, the detachment circuitry can include digital monitoring circuitry configured to monitor at least one data connection between the rechargeable battery and the processor when the rechargeable battery is attached to the battery-powered externally worn cardiac device.

In the device, the detachment circuitry can include analog monitoring circuitry configured to monitor for at least one of a voltage drop in the at least one battery cell and a current flow from the at least one battery cell.

In the device, the detachment circuitry can include at least one proximity detector configured to measure whether the rechargeable battery is attached to the battery-powered externally worn cardiac device. In some examples of the device, the at least one proximity detector can include at least one of a Hall Effect sensor, a light-based proximity sensor, a sound-based proximity sensor, a proximity switch, and a mechanical latching mechanism.

In the device, the audible and/or vibrational alarm circuitry can include at least one audio output device. In some examples of the device, the at least one audio output device can be adjustable to alter the predetermined frequency range of the audible alert. In some additional examples of the device, the at least one audio output device can be adjustable via a control provided during initial patient fitting of the battery-powered externally worn cardiac device. In some additional examples of the device, the at least one processor can be configured to adjust the predetermined frequency range based upon patient response to a hearing test administered by the battery-powered externally worn cardiac device during initial patient fitting of the battery-powered externally worn cardiac device. In some examples, the battery-powered externally worn cardiac device can further include a user interface configured to adjust the at least one audio output device. In some additional examples of the device, the user interface can include a mechanical interface configured to physically manipulate at least one component of the audible and/or vibrational alarm circuitry to adjust the at least one audio output device. In some additional examples of the device, the user interface can include a display configured to receive one or more inputs from a user of the battery-powered externally worn cardiac device to adjust the at least one audio output device.

In the device, the audible and/or vibrational alarm circuitry can include at least one output device operably coupled to and receiving power from the at least one battery cell, the at least one output device being configured to output the audible alert in a predetermined frequency range and/or the tactile alert.

In the device, the detachment circuitry can include a detachment processor configured to detect whether the rechargeable battery is detached from the battery-powered externally worn cardiac device and output the battery status signal.

In some examples, the battery-powered externally worn cardiac device can further include a plurality of sensing electrode configured to be coupled externally to a patient and to detect the one or more ECG signals of the patient wearing the battery-powered externally worn cardiac device.

In some examples, the battery-powered externally worn cardiac device can further include at least one therapy electrode configured to deliver one or more therapeutic shocks to a patient wearing the battery-powered externally worn cardiac device. In some additional examples of the device, the rechargeable battery can be configured to provide power to the at least one therapy electrode to deliver the one or more therapeutic shocks to the patient wearing the battery-powered externally worn cardiac device. In some additional examples of the device, the one or more therapeutic shocks can include defibrillation shocks.

In the device, the at least one battery cell can include three battery cells. In some examples of the device, at least one of the three battery cells is configured to provide power to the audible and/or vibrational alarm circuitry.

In the device, the audible and/or vibrational alarm circuitry can be further configured to output the audible alert in a predetermined frequency range and/or the tactile alert after a period of time has elapsed after the rechargeable battery is detached. In some examples of the device, the period of time can include at least one of one minute, two minutes, five minutes, ten minutes, fifteen minutes, twenty minutes, thirty minutes, one hour, and two hours. In some examples of the device, the period of time can include a user-programmable period of time.

In some examples, the battery-powered externally worn cardiac device can further include an alarm battery operably coupled to the audible and/or vibrational alarm circuitry and configured to provide power to the audible and/or vibrational alarm circuitry. In some additional examples of the device, the alarm battery can be removable to disable the audible and/or vibrational alarm circuitry. In some additional examples of the device, the alarm battery can be stored within a battery compartment in at least one of the housing and/or the rechargeable battery, the battery compartment being configured to open upon manipulation of a release mechanism.

In the device, the audible and/or vibrational alarm circuitry can be further configured to delay output of the audible alert in a predetermined frequency range and/or the tactile alert if the rechargeable battery is operably coupled to an external power supply.

In the device, the at least one signal indicating whether the rechargeable battery is detached from the battery-powered externally worn cardiac device can include at least one of a digital communication signal, an analog communication signal, a connection signal associated with one or more connection pins on the rechargeable battery, and a location signal indicating a physical location of the rechargeable battery.

In another example, a rechargeable battery for powering a battery-powered externally worn cardiac device is provided. The rechargeable battery includes at least one battery cell, detachment circuitry, and audible and/or vibrational alarm circuitry operably coupled to the detachment circuitry. The detachment circuitry is configured to detect whether the rechargeable battery is detached from the battery-powered externally worn cardiac device and output a battery status signal indicating whether the rechargeable battery is detached from the battery-powered externally worn cardiac device. The audible and/or vibrational alarm circuitry is configured to receive the battery status signal and output an audible alert in a predetermined frequency range and/or a tactile alert if the rechargeable battery is detached.

Implementations of the rechargeable battery for powering a battery-powered externally worn cardiac device can include one or more of the following features.

In examples of the rechargeable battery, the detachment circuitry can be further configured to determine whether the rechargeable battery is inserted into a battery charger by monitoring for a recharging current going from the battery charger to the at least one battery cell and output an updated battery status signal indicating whether the rechargeable battery is inserted into a battery charger. In additional examples of the rechargeable battery, the audible and/or vibrational alarm circuitry can be further configured to determine whether the rechargeable battery is inserted into a battery charger based upon the updated battery status signal and stop the output of the audible alert in a predetermined frequency range and/or the tactile alert if the rechargeable battery is inserted into a battery charger.

In the rechargeable battery, the detachment circuitry can include digital monitoring circuitry configured to monitor at least one data connection between the rechargeable battery and the processor of the battery-powered externally worn cardiac device when a rechargeable battery is attached to the battery-powered externally worn cardiac device.

In the rechargeable battery, the detachment circuitry can include analog monitoring circuitry configured to monitor for at least one of a voltage drop in the at least one battery cell and a current flow from the at least one battery cell.

In the rechargeable battery, the detachment circuitry can include at least one proximity detector configured to measure whether the rechargeable battery is attached to the battery-powered externally worn cardiac device.

In the rechargeable battery, the audible and/or vibrational alarm circuitry can include at least one audio output device. In some examples of the rechargeable battery, the at least one audio output device can be adjustable to alter the predetermined frequency range of the audible alert.

In another example, a battery charger for charging a rechargeable battery for powering a battery-powered externally worn cardiac device is provided. The battery charger includes a housing including at least a battery receiving portion, charging circuitry disposed within the housing, a power supply operably coupled to the charging circuitry, and battery detection circuitry. The charging circuitry is configured to removably couple to a rechargeable battery inserted into the battery receiving portion. The battery detection circuitry includes detachment circuitry and audible and/or vibrational alarm circuitry operably coupled to the detachment circuitry and the power supply. The detachment circuitry is configured to determine whether the rechargeable battery is at least one of inserted into the battery receiving portion and removably coupled to the charging circuitry and output a battery status signal indicating whether the rechargeable battery is at least one of inserted into the battery receiving portion and removably coupled to the charging circuitry. The audible and/or vibrational alarm circuitry is configured to receive the battery status signal and output at least one of an audible alert in a predetermined frequency range and a tactile alert if the rechargeable battery is at least one of not inserted into the battery receiving portion and not coupled to the charging circuitry.

Implementations of the battery charger for charging a rechargeable battery for powering a battery-powered externally worn cardiac device can include one or more of the following features.

In the battery charger, the detachment circuitry can be further configured to determine whether the rechargeable battery is inserted into a battery charger by monitoring for a recharging current going from the battery charger to at least one battery cell of the rechargeable battery and outputting an updated battery status signal indicating whether the rechargeable battery is inserted into the battery charger.

In the battery charger, the detachment circuitry can include at least one proximity detector configured to measure whether the rechargeable battery is attached to the battery-powered externally worn cardiac device.

In the battery charger, the audible and/or vibrational alarm circuitry can include at least one audio output device. In some examples of the battery charger, the at least one audio output device can be adjustable to alter the predetermined frequency range of the audible alert.

In another example, a battery-powered externally worn cardiac device with battery detachment detection is provided. The device includes a housing, at least one processor disposed in the housing, a rechargeable battery removably coupled to the at least one processor, and a battery detection circuit. The at least one processor is configured to process one or more ECG signals of a patient wearing the battery-powered externally worn cardiac device and determine at least one arrhythmia based on the processed ECG signal. The battery detection circuit includes at least one battery cell, detachment circuitry, and audible and/or vibrational alarm circuitry operably coupled to the detachment circuitry. The detachment circuitry is configured to determine whether the rechargeable battery is attached to the battery-powered externally worn cardiac device and output a battery status signal indicating whether the rechargeable battery is attached to the battery-powered externally worn cardiac device. The audible and/or vibrational alarm circuitry is configured to receive the battery status signal and output an audible alert in a predetermined frequency range and/or a tactile alert if the rechargeable battery is detached.

Implementations of the battery-powered externally worn cardiac device with battery detachment detection can include one or more of the following features.

In the device, the detachment circuitry can include digital monitoring circuitry configured to monitor at least one data connection between the rechargeable battery and the processor when the rechargeable battery is attached to the battery-powered externally worn cardiac device.

In the device, the detachment circuitry can include analog monitoring circuitry configured to monitor for at least one of a voltage drop in the at least one battery cell and a current flow from the at least one battery cell.

In the device, the detachment circuitry can include at least one proximity detector configured to measure whether the rechargeable battery is attached to the battery-powered externally worn cardiac device.

In the device, the audible and/or vibrational alarm circuitry can include at least one audio output device. In some examples of the device, the at least one audio output device is adjustable to alter the predetermined frequency range of the audible alert.

In the device, the at least one battery cell can be configured to provide power to at least one of the detachment circuitry and the audible and/or vibrational alarm circuitry. In some examples of the device, the housing can include a user-accessible battery compartment configured to house the at least one battery cell and provide access to the at least one battery cell for removal of the at least one battery cell to disconnect power to at least one of the detachment circuitry and the audible and/or vibrational alarm circuitry.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
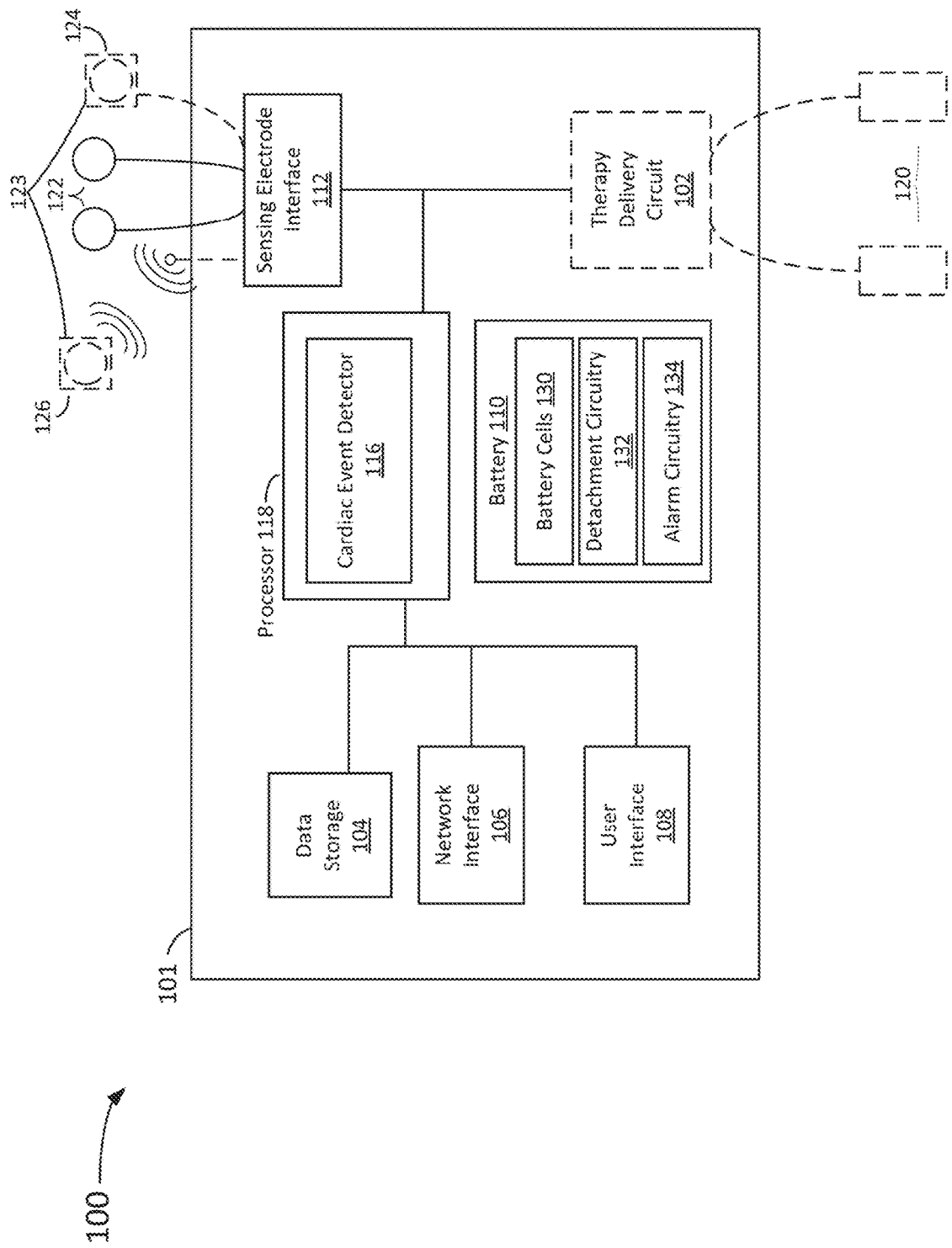
FIG. 1 illustrates a schematic view of a sample controller for a wearable medical device, in accordance with an example of the present disclosure.

Wearable medical devices, such as cardiac event monitoring and treatment devices, are used in clinical or outpatient settings to monitor and/or record various ECG and other physiological signals for a patient. These ECG and other physiological signals can be used to determine a current condition for a patient as well as to provide an indication that the patient may require treatment such as a defibrillation shock.

Wearable medical devices are powered by either an integrated rechargeable battery or by a removable rechargeable battery. Where a patient is required to wear a WCD for a majority of the day (e.g., only to removed when bathing), it may not be practical to prescribe a device that includes an integrated rechargeable battery. Instead, the patient can be given two rechargeable batteries and instructed to insert one battery in the medical device, to insert the second battery into the charger, and to swap the batteries when the remaining runtime of the battery in the medical device drops below a threshold value. When the batteries are to be swapped, the first battery is removed from the WCD and temporarily placed aside. The second battery is removed from the charger and inserted into the WCD. Once the WCD has restarted and is being properly powered by the second battery, the patient places the first battery onto the charger for charging. By following these instructions, when a battery swap is required (e.g., every 24 hours), a fully charged battery is sitting in the charger and ready to power the WCD.

Failure to follow these instructions can cause several problems. For example, if the patient forgets to place a depleted battery onto the charger, when time for the next battery swap arrives the patient will not have a charged battery to insert into the medical device. Such a scenario can result in the medical device not functioning properly or at all. For example, with a WCD, providing a treatment or therapy shock to the patient requires significantly more power than merely providing monitoring of the patient's physiological signals. So, while the WCD may continue to monitor the patient with a depleted battery, it may fail to provide an adequate treatment shock if the patient is experiencing, for example, ventricular fibrillation (VF). Such an occurrence can result in a life-threatening situation for the patient.

To address these and other obstacles to successful execution of, and patient adherence to, battery replacement and charging instructions, systems and process for providing a battery removal alert are described herein. For example, a rechargeable battery for a wearable medical device such as a WCD can include detachment circuitry configured to monitor whether the rechargeable battery is properly inserted into either the wearable medical device or a battery charger. For example, the detachment circuitry can be configured to determine whether the rechargeable battery is physically inserted into the wearable medical device or battery charger. In other examples, the detachment circuitry can be configured to determine whether current is flowing out of the rechargeable battery (e.g., the rechargeable battery is inserted into and powering the wearable medical device) or whether current is flowing into the rechargeable battery (e.g., the rechargeable battery is inserted into the charger and is being charged). The rechargeable battery can also include alarm circuitry operably coupled to the detachment circuitry. The alarm circuitry is configured to output an alert or alarm if the detachment circuitry provides an indication that the rechargeable battery is not properly inserted into the wearable medical device or battery charger.

For example, a rechargeable battery for powering a battery-powered externally worn cardiac device can include at least one battery cell; detachment circuitry, and audible and/or vibrational alarm circuitry operably coupled to the detachment circuitry. The detachment circuitry can be configured to detect whether the rechargeable battery is detached from the battery-powered externally worn cardiac device and output a battery status signal indicating whether the rechargeable battery is detached from the battery-powered externally worn cardiac device. The audible and/or vibrational alarm circuitry can be configured to receive the battery status signal and output an audible alert in a predetermined frequency range and/or a tactile alert if the rechargeable battery is detached.

In a similar example, a battery-powered externally worn cardiac device can include a housing. The housing can include at least one processor and a rechargeable battery. The rechargeable battery can be detachable from the housing and removably coupled to the at least one processor. The rechargeable battery can include at least one battery cell, detachment circuitry, and audible and/or vibrational alarm circuitry operably coupled to the detachment circuitry. The processor can be configured to process one or more ECG signals of a patient wearing the battery-powered externally worn cardiac device and to determine at least one arrhythmia based on the processed ECG signal.

In such examples as those described above, an individual rechargeable battery can be configured to provide feedback directly to the patient as to whether the patient is properly following directions regarding battery replacement and charging. For example, the alarm circuitry in the rechargeable battery can be configured to provide an audible or tactile alert if the rechargeable battery is not properly placed in the medical device or the battery charger. Thus, improper swapping of batteries due to patient mistakes can be reduced or eliminated.

In addition to or alternatively to providing detachment and alarm circuitry in the rechargeable battery, circuitry that performs a similar function can be included in, for example, the battery charger. By providing such circuitry in the battery charger, a patient can be alerted by an alternate or additional source when a rechargeable battery is not properly inserted into the battery charger. As noted above, a patient can be given two rechargeable batteries with a wearable medical device and be instructed to keep one rechargeable battery in the medical device at all times and to keep one rechargeable battery in the charger at all times. As noted above, such a procedure ensures that a rechargeable battery is fully charged when time for a battery swap.

In an example, a battery charger for charging a rechargeable battery for powering a battery-powered externally worn cardiac device can include a housing including at least a battery receiving portion, charging circuitry disposed within the housing, and battery detection circuitry. The charging circuitry can be configured to removably couple to a rechargeable battery inserted into the battery receiving portion, a power supply operably coupled to the charging circuitry, and battery detection circuitry. The battery detection circuitry can include detachment circuitry and audible and/or vibrational alarm circuity operably coupled to the detachment circuitry and the power supply. The detachment circuitry can be configured to determine whether the rechargeable battery is at least one of inserted into the battery receiving portion and removably coupled to the charging circuitry and output a battery status signal indicating whether the rechargeable battery is at least one of inserted into the battery receiving portion and removably coupled to the charging circuitry. The audible and/or vibrational alarm circuitry operably can be configured to receive the battery status signal and output at least one of an audible alert in a predetermined frequency range and a tactile alert if the rechargeable battery is at least one of not inserted into the battery receiving portion and not coupled to the charging circuitry.

In such an example, providing alarm circuitry in the battery charger can provide a redundant notification to the patient if the patient has forgotten to place a rechargeable battery into the battery charger. Such a design can help to eliminate the risk of having a rechargeable battery that is not charged when time to swap batteries. Such a design also provides for the use of legacy or older rechargeable batteries that do not include detachment and alarm circuitry as described herein.

In certain circumstances, the patient may make other errors or mistakes when changing the battery. For example, the patient may become distracted and forget to re-insert a battery into the medical device when swapping batteries. The patient may then leave their home without a battery in the medical device, thereby rendering the life-saving capabilities of the medical device as useless. To prevent such a potential problem, the medical device controller itself can include detachment and alarm circuitry as described herein.

In such an example, a battery-powered externally worn cardiac device can include medical device controller. The medical device controller can include a housing, at least one processor, a battery chamber disposed within the housing to receive a rechargeable battery, a rechargeable battery, and a battery detection circuit disposed in the housing of the controller. The at least one processor can be configured to process one or more ECG signals of a patient wearing the battery-powered externally worn cardiac device and determine at least one arrhythmia based on the processed ECG signal. The rechargeable battery can be removably coupled to the at least one processor. The battery detection circuit can include at least one battery cell or other similar power supply, detachment circuitry, audible and/or vibrational alarm circuitry operably coupled to the detachment circuitry. The detachment circuitry can be configured to determine whether the rechargeable battery is attached to the battery-powered externally worn cardiac device and output a battery status signal indicating whether the rechargeable battery is attached to the battery-powered externally worn cardiac device. The audible and/or vibrational alarm circuitry can be configured to receive the battery status signal and output an audible alert in a predetermined frequency range and/or a tactile alert if the rechargeable battery is detached.

In such an example, an alternative or additional alert can be provided to the patient if the patient has forgotten to reinsert a rechargeable battery into their medical device. Such an example is advantageous if the patient is leaving their house where they may not hear an alert coming from the rechargeable battery and/or battery charger as described above.

These examples, and various other similar examples of benefits and advantages of the techniques, processes, and approaches as provided herein, are described in additional detail below.

The various dynamic adjustment and adherence monitoring processes described herein are implemented, in some examples, by data processing devices, such as computer systems and certain types of medical devices. For instance, some examples include a patient monitoring and treatment device. Patient monitoring and treatment devices are used to monitor and record various physiological or vital signals for a patient and provide treatment to a patient when necessary. For patients at risk of a cardiac arrhythmia, specialized cardiac monitoring and/or treatment devices such as a cardiac event monitoring device, a WCD, or a hospital wearable defibrillator can be prescribed to and worn by the patient for an extended period of time. For example, a patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed a specialized cardiac monitoring and/or treatment device.

For example, a WCD such as the LifeVest® Wearable Cardioverter Defibrillator from ZOLL Medical Corporation (Chelmsford, MA), can be prescribed to the patient. As described in further detail below, such a device includes a garment that is configured to be worn about the torso of the patient. The garment can be configured to house various components such as ECG sensing electrodes and therapy electrodes. The components in the garment can be operably connected to a monitoring device that is configured to receive and process signals from the ECG sensing electrodes to determine a patient's cardiac condition and, if necessary, provide treatment to the patient using the therapy electrodes.

FIG. 1 illustrates an example component-level view of the medical device controller 100 included in, for example, a wearable medical device such as a WCD. As shown in FIG. 1, the medical device controller 100 can include a housing 101 configured to house a therapy delivery circuitry 102 configured to provide one or more therapeutic shocks to the patient via at least two therapy electrodes 120, a data storage 104, a network interface 106, a user interface 108, at least one rechargeable battery 110 (e.g., within a battery chamber configured for such purpose), a sensor interface 112 (e.g., to interface with both ECG sensing electrodes 122 and non-ECG physiological sensors 123 such as motion sensors, vibrational sensors, lung fluid sensors, infrared and near-infrared-based pulse oxygen sensor, blood pressure sensors, among others), a cardiac event detector 116, and least one processor 118.

In some examples, the patient monitoring medical device can include a medical device controller 100 that includes like components as those described above but does not include the therapy delivery circuitry 102 and the therapy electrodes 120 (shown in dotted lines). That is, in certain implementations, the medical device can include only ECG monitoring components and not provide therapy to the patient. In such implementations, the construction of the patient monitoring medical device is similar in many respects as a WCD medical device controller 100 but need not include the therapy delivery circuitry 102 and associated therapy electrodes 120.

As further shown in FIG. 1, the rechargeable battery 110 can include various other components as described herein. For example, the rechargeable battery 110 can include one or more battery cells 130, detachment circuitry 132, and alarm circuitry 134. The rechargeable battery 110 is described in additional detail in the following discussion of FIG. 2 through FIG. 4F. FIG. 1 is described in greater detail below.

Figure 2:
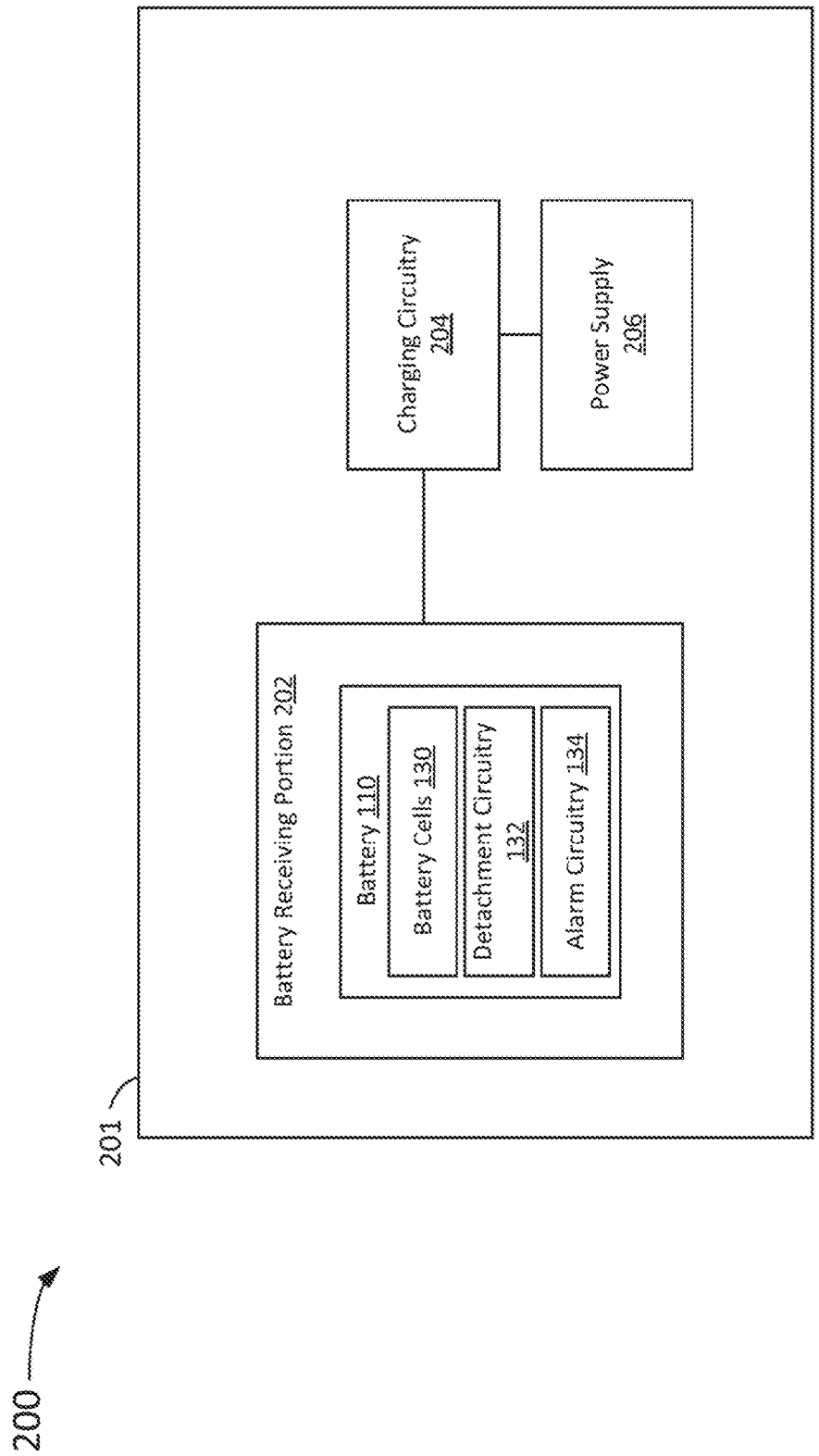
FIG. 2 illustrates a schematic view of a battery charger for a rechargeable battery for a wearable medical device, in accordance with an example of the present disclosure.

FIG. 2 illustrates an example component-level view of a battery charger 200 included with, for example, a wearable medical device such as a WCD when the medical device is prescribed to a patient. As shown in FIG. 2, the battery charger 200 can include a housing 201 configured to house various components of the battery charger. For example, the housing 201 can be configured to include a battery receiving portion 202. The battery receiving portion 202 can include a recessed or similarly shaped cavity configured to physically receive at least a portion of the rechargeable battery 110. The battery receiving portion 202 can further include one or more electrical connectors configured to establish an electrical connection between the rechargeable battery 110 and charging circuitry 204. The charging circuitry 204 can include various electrical components arranged to condition power received from a power supply 206 into electrical signals suitable for charging the rechargeable battery 110. For example, the power supply 206 can be a plug or other similar connector configured to plug into an electrical wall outlet and receive main power at, for example, 120 volts and 10 amps. The charging circuitry 204 can be configured to convert the main power to a level suitable for charging the rechargeable battery 110. For example, the charging circuitry 204 can be configured to convert the main power to about 5 volts at about 2.5 amps.

Similar to FIG. 1, rechargeable battery 110 as shown in FIG. 2 includes additional components such as one or more battery cells 130, detachment circuitry 132, and alarm circuitry 134.

Figure 3:
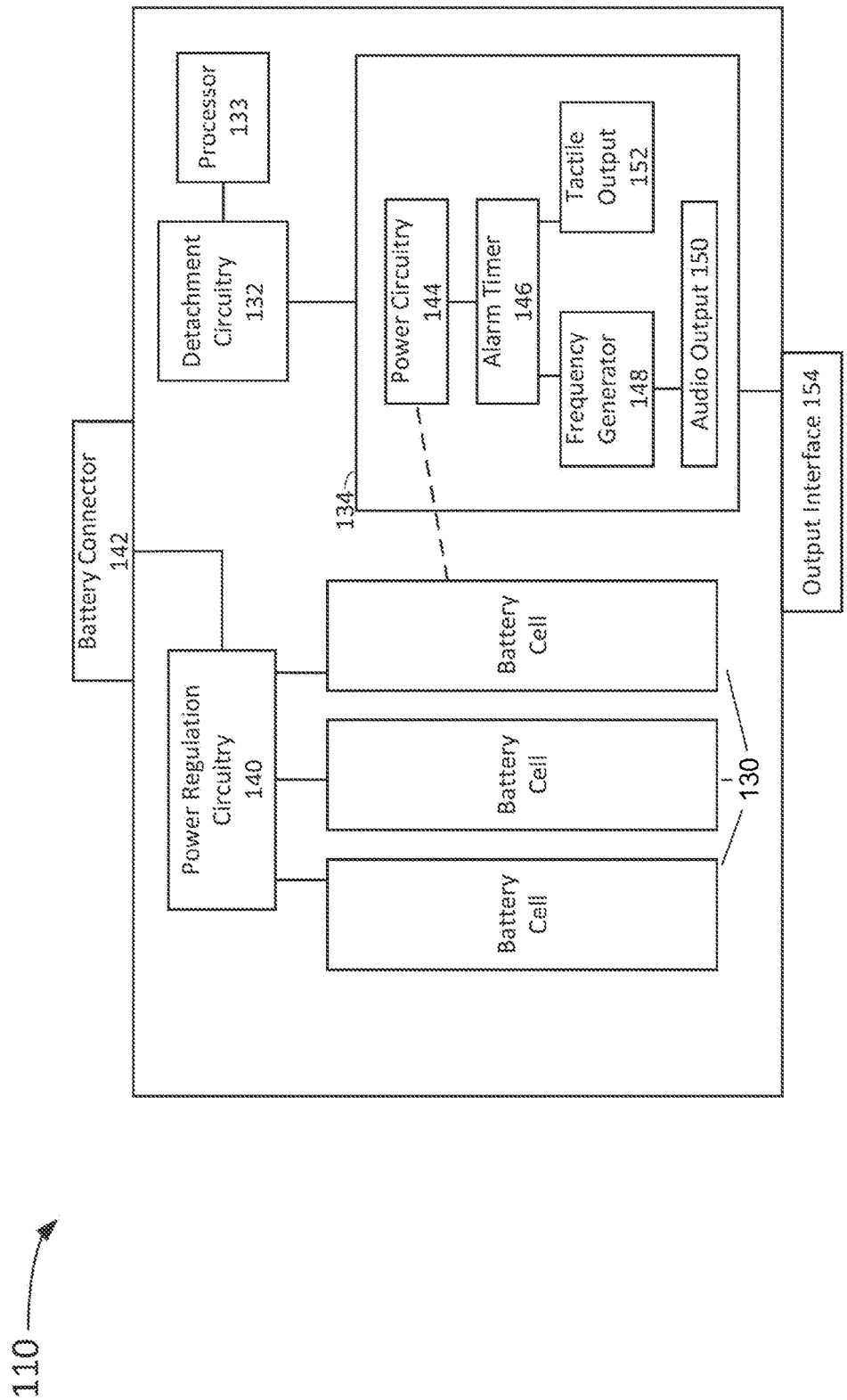
FIG. 3 illustrates a schematic view of a rechargeable battery including detachment circuitry and alarm circuitry, in accordance with an example of the present disclosure.

FIG. 3 illustrates a more detailed view of rechargeable battery 110. For example, as shown in FIG. 3, the rechargeable battery 110 can include a set of battery cells 130. As shown in FIG. 3, three battery cells 130 as provided by way of example only. Depending upon the design of the rechargeable battery 110, and the expected power output requirements of the rechargeable battery, the number of battery cells 130 can be varied. For example, the rechargeable battery 110 can include two battery cells 130, four battery cells, six battery cells, nine battery cells, and other similar quantities of battery cells.

As further shown in FIG. 3, the rechargeable battery 110 can further include power regulation circuitry 140. The power regulation circuitry 140 can be configured to condition and provide power to another device such as a wearable medical device as described herein via battery connector 142. Conversely, during charging, the power regulation circuitry 140 can be configured to receive power from the battery charger via the battery connector 142 and, if necessary, condition the power for charging the power cells 130. As also shown in FIG. 3, the detachment circuitry 132 can include or be operably coupled to a processor 133. For example, the processor 133 can be configured to monitor one or more components of the detachment circuitry 132 and to output, for example, a battery status signal to the alarm circuitry 134 as described in greater detail below. It should be noted that a processor 133 is shown by way of example only and, in certain implementations, additional control circuitry such as programmable digital logic controls can be used to monitor and provide control to the detachment circuitry 132 as described herein.

Additionally, FIG. 3 provides added detail for the alarm circuitry 134 as described herein. In certain implementations, the alarm circuitry 134 can be configured to provide one or more of an audible alert and/or a tactile alert to a patient. For example, the alarm circuitry 134 can include power circuitry 144 that is operably connected to one or more of the battery cells 130 and configured to provide power to the other components as contained within the alarm circuitry 134.

The alarm circuitry 134 can also include an alarm timer 146. The alarm timer 146 can be configured to provide timing information for an output of the alarm circuitry 134. For example, the alarm timer 146 can be operably coupled to the power circuitry 144 and configured to provide an electrical signal to one or more output devices such that the alerts generated by the output devices occur after expiration of a predetermined period of time. For example, the alarm timer 146 can be configured such that the alarm circuitry 134 as described herein outputs one or more alerts after the predetermined period of time has passed since the rechargeable battery 110 has been removed from a medical device or a battery charger. In certain implementations, the alarm timer 146 can include a capacitor configured to discharge over the predetermined period of time. Upon total discharge of the capacitor, the alarm timer 146 can provide an indication that the predetermined period of time has expired. The capacitor can be charged to a value based on the predetermined period of time set in accordance with initial configuration of the device. In other implementations, the alarm timer 146 can include a digital timer configured to output a signal after the predetermined period of time has elapsed. For example, the predetermined period of time measured by the alarm timer 146 can be one minute, two minutes, five minutes, ten minutes, fifteen minutes, twenty minutes, thirty minutes, one hour, two hours, and other periods of time. In implementations, the predetermined period of time can be set based on a configurable parameter accessible to an authorized person via a user interface of the medical device. For example, such a configurable parameter may also be remotely set at a remote server and transmitted via a wireless communication interface (e.g., Wi-Fi™, Bluetooth®, or other wireless network interface) to the medical device controller.

In an example, the alarm timer 146 can provide timing information indicating how long an alert is to be output. As an example, if the alert is an audible and/or vibrational alert, an additional degree of configuration can be provided to allow for having the audible alert to automatically shut off after a predetermined alarm period has elapsed. For example, to conserve battery power, the alarm circuitry 134 can be configured to provide an alert to the patient that the rechargeable battery 110 has been removed from a medical device or a battery charger for the predetermined alarm period. Upon expiration of the predetermined alarm period, the alarm circuitry 134 can stop outputting the alert. For example, the alarm period of time can be one minute, two minutes, five minutes, ten minutes, fifteen minutes, twenty minutes, thirty minutes, one hour, two hours, and other periods of time. In some implementations, the predetermined alarm period can be set based on a configurable parameter accessible to an authorized person via a user interface of the medical device. For example, such configurable parameter may also be remotely set at a remote server and transmitted via a wireless communication interface (e.g., Wi-Fi™, Bluetooth®, or other wireless network interface) to the medical device controller. In some implementations, in addition to or alternative to stopping the alert, the device can be configured to suspend the alert for a second predetermined suspended alarm period. For example, such a predetermined suspended alarm period can be one minute, two minutes, five minutes, ten minutes, fifteen minutes, twenty minutes, thirty minutes, one hour, two hours, and other periods of time. In some implementations, the predetermined suspended alarm period can also be set based on a configurable parameter accessible to an authorized person via a user interface of the medical device, or remotely via a wireless communication interface.

In certain implementations, after the predetermined period of time has elapsed, the alarm timer 146 can send a signal to one or more output devices to generate an alert. For example, as shown in FIG. 3, the alarm circuitry 134 can include a frequency generator 148 and an audio output 150 configured to produce and output a particular audible alert. As described herein, the audio output 150 can include a device configured to provide an audible output such as a speaker. In certain implementations, the audible alert can have a predetermined frequency range based upon, for example, the hearing capabilities of the patient. Setting a predetermined frequency range is described in greater detail below.

In addition to the audio output 150, the alarm circuitry 134 can further include a tactile output 152. For example, the tactile output 152 can include a haptic feedback device configured to cause a vibration or a series of vibrations at a certain frequency and force.

In certain implementations, the battery 110 can include a user interface such as an output interface 154. The output interface 154 can be a mechanical interface such as a sliding switch, a rotating dial, or other similar mechanical interface that a patient or someone assisting the patient can use to alter the output of the alarm circuitry 134. For example, the output interface 154 can be a sliding switch configured to alter the output volume and/or frequency of the audio output 150. In implementations, the output interface 154 can be used to allow the user to modify any one of the alarm time periods described above, including the predetermined period of time before an alarm is initiated, the predetermined alarm period indicating duration of the alarm, and the predetermined suspended alarm period.

Depending upon the design of the rechargeable battery 110, the medical device controller 100, and the charger 200, the detachment circuitry 132 as described herein can be designed and implemented in various manners. For example, Table 1 as shown below outlines design types for implementing the detachment circuitry 132 as well as brief function summary and a commercial example, each type being described in greater detail below with reference to one or more of FIGS. 4A-4F.

TABLE 1

| DETECTION CIRCUITRY TYPE | FUNCTION |
|---|---|
| Digital I/O Monitoring | Monitor connection bus between battery and monitor/controller for data transfer |
| Analog I/O Monitoring | Measure for active discharge of battery cells or current flow from battery cells |
| Hall Effect Sensor | Measure magnetic field generated by a portion of the monitor/controller to determine if battery is inserted into monitor/controller Example device: Texas Instruments DRV5053 |
| Optical Sensor | Use imaging such as infrared-based proximity detection to determine if battery is inserted into monitor/controller Example devices: Sharp GP2Y0D805Z0F, Everlight EAITRAA1 (transmissive) |
| Ultrasonic Sensor | Use ultrasonic sound detection to determine if battery is inserted into monitor/controller Example device: Baumer UNCK 09G8914/IO |
| Proximity Switch | Physical interface that detects physical presence of the monitor/controller as a result of displacement of at least a portion of the switch Example device: Panasonic ESE22 Detector Switches |
| Battery Latch | Physical interface that is manually or automatically displaced when the battery is inserted into the monitor/controller and may remain at least partially displaced when properly inserted Example device: Crouzet M30 CPM723015C |
| Dedicated Electrical Connection Monitor | A dedicated pin on the Battery/Monitor electrical connector. |
| Magnetic reed switch | Switch changes condition/position when battery is inserted. |

For example, as listed in Table 1, the detachment circuitry can include digital input/output (I/O) monitoring. The digital I/O monitoring can include monitoring a connection such as an electrical bus between the medical device controller and the rechargeable battery, or the battery charger and the rechargeable battery, to determine if the rechargeable battery is properly inserted and electrically coupled to either the medical device controller or the battery charger.

Figure 4A:
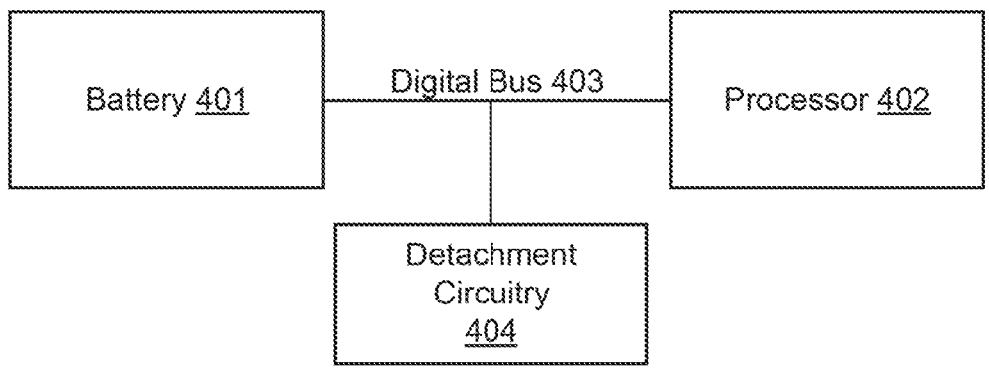
FIGS. 4A-4F illustrate schematic views of various examples of detachment circuitry, in accordance with various examples of the present disclosure.

For example, as shown in FIG. 4A, a rechargeable battery 401 can be electrically coupled to a processor 402 of a wearable medical device controller via a digital bus 403. The detachment circuitry 404 can monitor one or more lines in the electrical bus 403 for activity indicative of a connection between the rechargeable battery 401 and the processor 402. For example, the electrical bus 403 can include a status line that is high when the rechargeable battery 401 is connected to the processor 402 and, conversely, is low when there is no connection. A detachment circuitry 404 can be configured to monitor the status line condition to determine whether an electrical connection is established between the rechargeable battery 401 and the processor 402.

In another example as listed in Table 1, the detachment circuitry can include monitoring for analog signals between the medical device controller and the rechargeable battery, or the battery charger and the rechargeable battery, to determine if the rechargeable battery is properly inserted and electrically coupled to either the medical device controller or the battery charger.

Figure 4B:
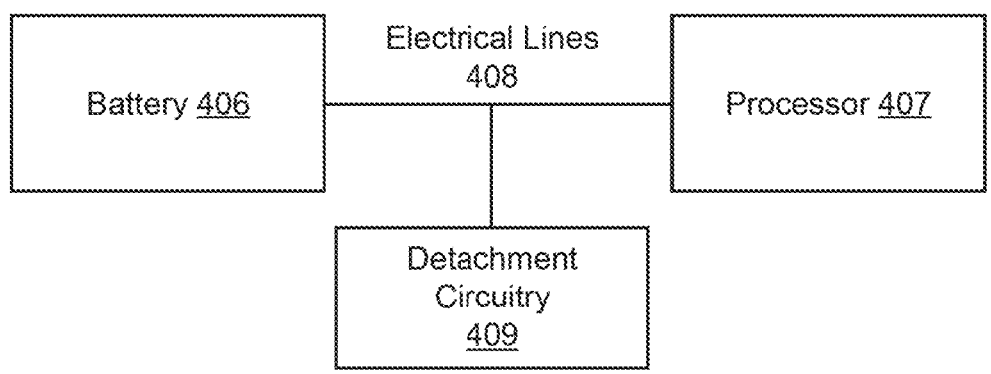

For example, as shown in FIG. 4B, a rechargeable battery 406 can be electrically coupled to a processor 407 of a wearable medical device controller via one or more electrical lines 408. A detachment circuitry 409 can monitor one or more lines in the electrical lines 408 for activity indicative of a connection between the rechargeable battery 406 and the processor 407. For example, the detachment circuitry 409 can be configured to monitor the electrical lines 408 to monitor for current flow from the rechargeable battery 406 to the processor 407, thereby providing an indication that the rechargeable battery and the processor are electrically coupled.

In addition to monitoring circuitry configured to monitor for a digital or analog signal that can be indicative of a connection between a rechargeable battery and a wearable medical device controller or battery charger, the detachment circuitry can further include one or more physical sensors and/or detection mechanisms for determining if a rechargeable battery is properly inserted into another device.

In another example as shown in Table 1, the detachment circuitry can include a Hall Effect sensor that is configured to measure a magnetic field generated by, for example, a magnet that is positioned adjacent to a position where the rechargeable battery is inserted into the wearable medical device controller or battery charger. For example, a magnet can be integrated into the housing 201 of the battery charger near the battery receiving portion 202 as described above. Upon insertion of the rechargeable battery into the battery receiving portion 202, the Hall Effect sensor included in the detachment circuitry as described herein can measure the magnetic field as generated by the magnet, thereby providing an indication that the rechargeable battery is properly inserted into the battery charger or the wearable medical device controller.

Other powered proximity-type sensors are also included in Table 1. For example, the detachment circuitry can include an optical sensor such as an infrared proximity detector that is configured to measure a distance between a portion of the rechargeable battery and a portion of the wearable medical device controller and/or battery charger. Another proximity-type sensor as shown in Table 1 includes an ultrasonic sensor that is configured to emit an ultrasonic sound and measure reflected sound waves to determine whether a rechargeable battery is properly inserted into a wearable medical device controller and/or a battery charger.

Figure 4C:
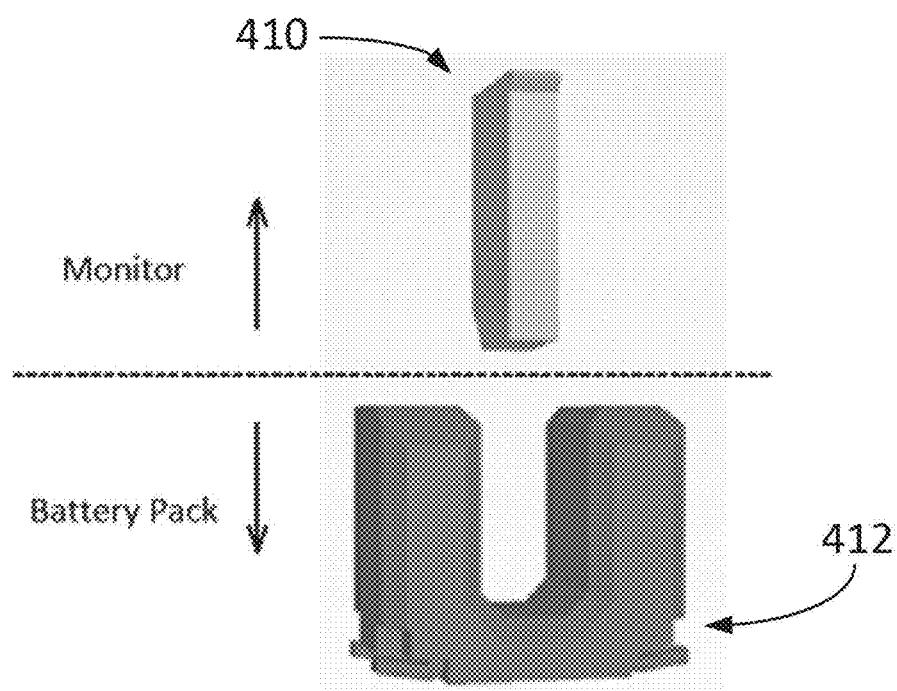

FIG. 4C illustrates an example of various powered proximity sensors such as the Hall Effect sensor, optical sensor, and ultrasonic sensor as described above. For example, the wearable medical device controller can include a detectable feature 410 such as a protruding piece of the housing of the controller. The rechargeable battery can also include a sensor 412 such as a Hall Effect sensor, an optical sensor, and an ultrasonic sensor as described herein and listed in Table 1. If the sensor 412 is a Hall Effect sensor, the detectable feature 410 of the medical device controller can include a magnet. If the sensor 412 is an optical sensor, the detectable feature 410 of the medical device controller can include one or more reflective surfaces configured to reflect any light emitted by the optical sensor. If the sensor 412 is an ultrasonic sensor, the detectable feature 412 can be made of a sonically reflective material that is shaped to reflect sound emitted by the ultrasonic sensor back at the sensor.

In addition to powered proximity-type sensors, the detachment circuitry can include mechanical proximity-type sensors as well. For example, the detachment circuitry can include a proximity switch that is at least partially depressed or otherwise displaced when the rechargeable battery is inserted into, for example, a wearable medical device controller. In another example, another mechanical proximity interface can include a battery latch that is depressed by the patient when inserting the rechargeable battery. In certain implementations, at least a portion of the battery latch can remain displaced when the rechargeable battery is properly inserted into the wearable medical device controller. In both examples, the detachment circuitry can include a switch that is directly connected to the proximity switch or battery latch, and the status of the switch (e.g., opened or closed) can provide a direct indication of whether the rechargeable battery is properly inserted into the wearable medical device controller.

Figure 4D:
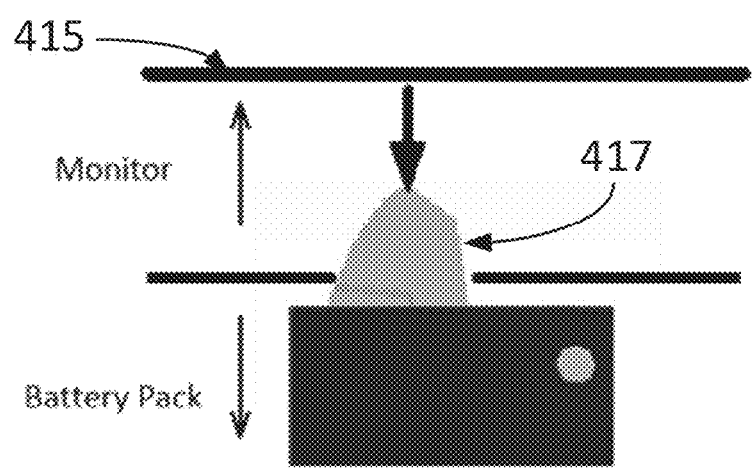

For example, FIG. 4D illustrates a sample mechanical proximity switch. As the rechargeable battery is inserted into the wearable medical device controller, a portion 415 of the controller can be positioned to depress a proximity switch 417 on the rechargeable battery. While the rechargeable battery remains properly inserted in the controller, the proximity switch 417 remains at least partially depressed as described above.

Another detachment circuitry type as noted in Table 1 can include a dedicated electrical connection monitor. For example, the monitor can be configured to detect a signal on a dedicated pin on the connector between the rechargeable battery and the wearable medical device controller. In certain implementations, the dedicated pin can provide a loop-back function that provides a signal to the rechargeable battery that there is an electrical connection with the controller. When implemented, the dedicated electrical connection monitor can be configured to confirm via measurement that an electrical connection has been made between the rechargeable battery and the wearable medical device controller.

Figure 4E:
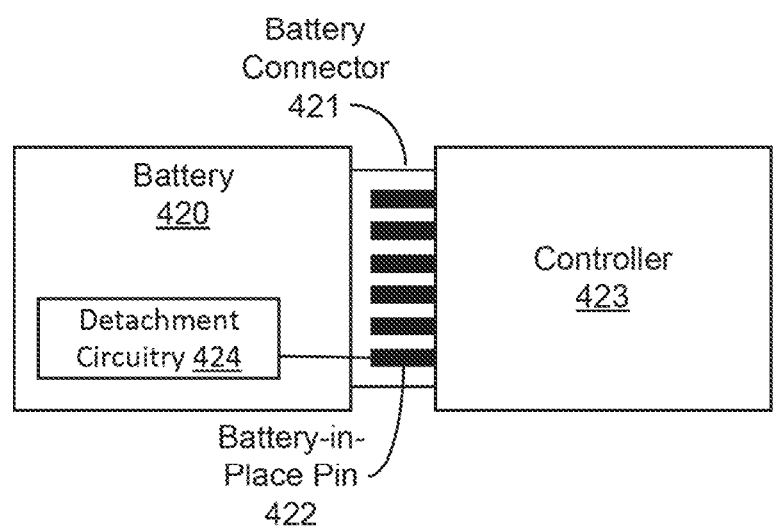

For example, as shown in FIG. 4E, a rechargeable battery 420 can be electrically connected to a controller 423 via a battery connector 421. The battery connector 421 can include at least one battery-in-place pin 422 that is monitored by detachment circuitry 424. As noted above, the detachment circuitry 424 can monitor for any changes in the output of the battery-in-place pin and, upon detecting a change, provide an indication to the alarm circuitry as described herein.

Figure 4F:
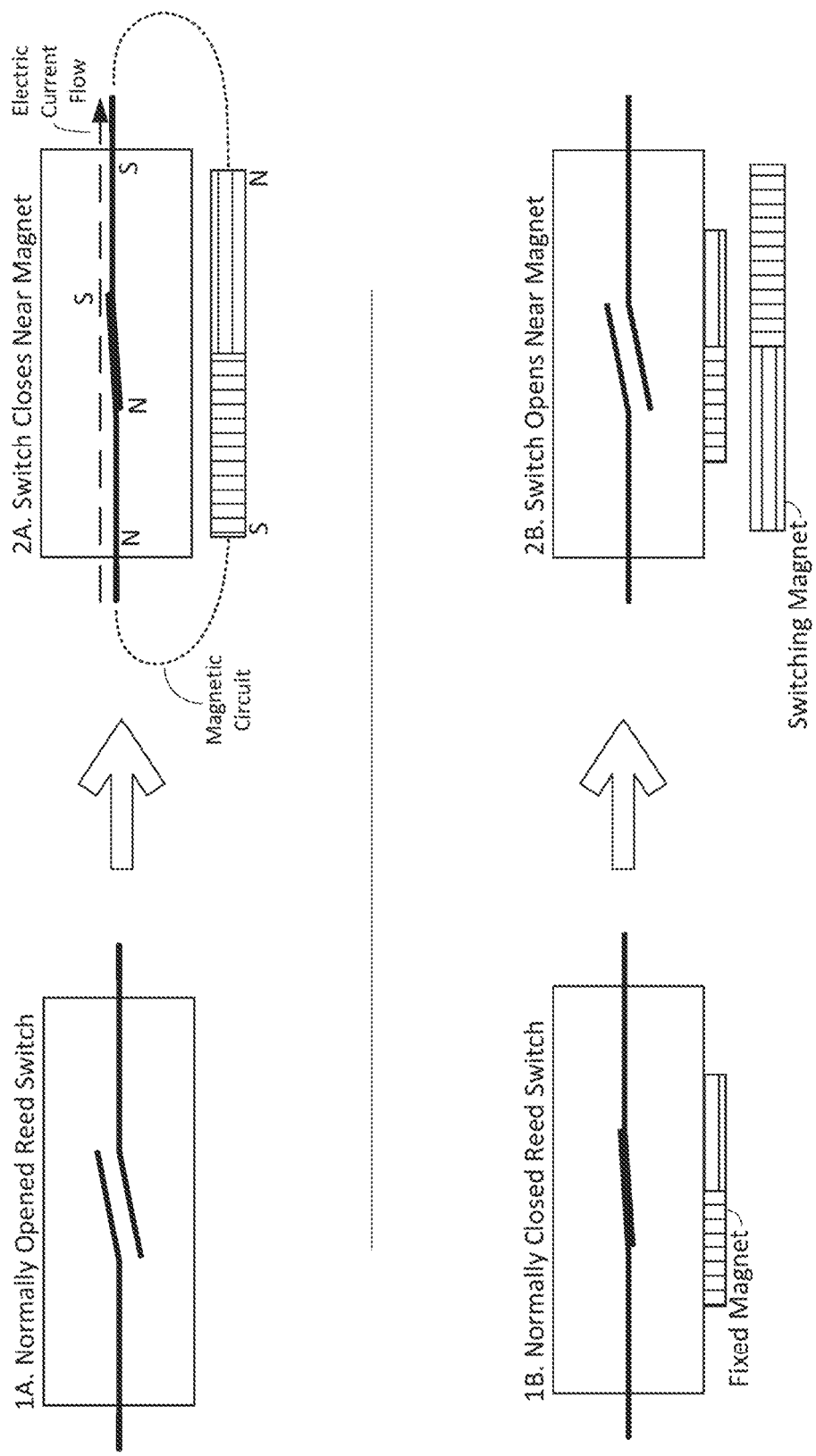

Another detachment circuitry example can be the use of a mechanical switch such as a reed switch that reacts to the presence of, for example, a magnet. Rather than use a powered sensor such as Hall Effect sensor, a reed switch provides for a mechanical solution. For example, as shown in FIG. 4F, a reed switch can be normally open or normally closed. When in proximity of a magnet, the normally open reed switch moves to a closed state and, conversely, the normally closed reed switch moves to an open state. Such a switch can be integrated into the detachment circuitry as described herein to provide an additional type of mechanical detachment detection.

It should be noted that, in the above examples, when determining a connection between a rechargeable battery and a wearable medical device controller is discussed, the same concepts and techniques can be used to determine a connection between the rechargeable battery and a battery charger. Conversely, in the above examples, when determining a connection between a rechargeable battery and a battery charger is discussed, the same concepts and techniques can be used to determine a connection between the rechargeable battery and a wearable medical device controller.

Figure 5:
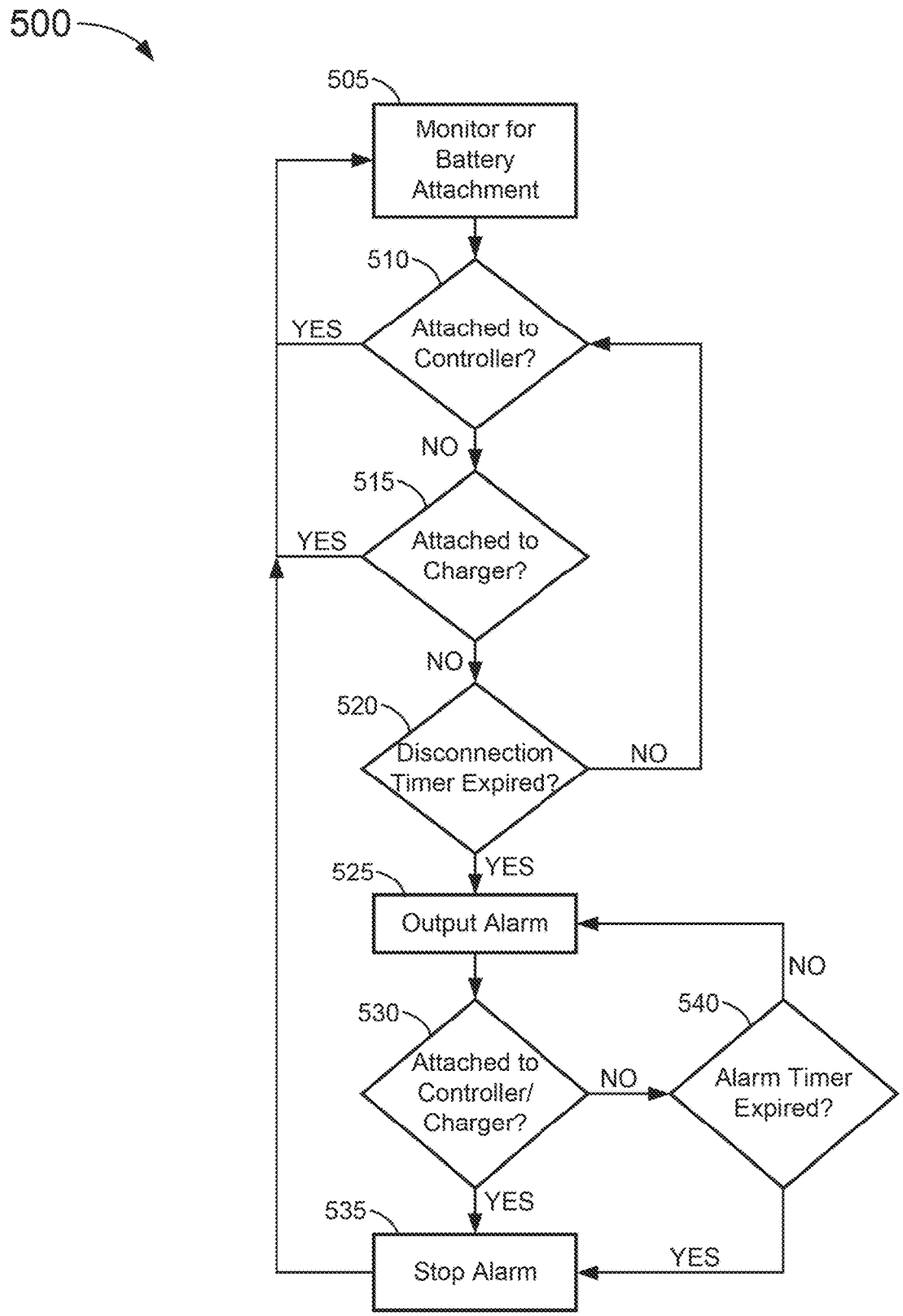
FIG. 5 illustrates a process flow for monitoring battery attachment and providing an alarm if detached, in accordance with an example of the present disclosure.

FIG. 5 illustrates a sample process 500 for operating alarm circuitry when integrated into a rechargeable battery as described above. In certain implementations, the detachment circuitry as described herein can include a processor (e.g., processor 133 as described above) or other similar computing device that is configured to perform a set of instructions to perform a process such as process 500 as described herein. For example, the processor can monitor 505 for battery attachment. For example, the rechargeable battery can include one or more of the detachment circuit types as listed in Table 1 and described above.

In certain implementations, the processor can monitor one or more connections between the rechargeable battery and the wearable medical device for the presence or status of one or more signals that can be indicative of a connection between the rechargeable battery and the wearable medical device controller. Examples of such signals indicative of a connection can include a digital communication signal (e.g., as outlined in FIG. 4A and described above), an analog communication signal (e.g., as outlined in FIG. 4B and described above), an electrical connection signal associated with, for example, one or more connection pins of the rechargeable battery (e.g., as shown in FIG. 4E and described above), and a location signal indicating a physical location of the rechargeable battery (e.g., as shown in FIGS. 4C, 4D, and 4F and described above).

As further shown in FIG. 5, the output of the detachment circuit can be monitored 505 and one or more determinations can be made. For example, the processor can determine 510 whether the rechargeable battery is properly attached to the wearable medical device controller. If the processor does determine 510 that the rechargeable battery is properly attached to the controller, the processor can continue to monitor 505 for battery attachment. If the processor does not determine 510 that the rechargeable battery is attached to the controller, the processor can determine 515 if the rechargeable battery is attached to the battery charger. If the processor determines 515 that the battery is attached to the battery charger, the processor can continue to monitor 505 for battery attachment.

If the processor determines 515 that the rechargeable battery is not connected to the battery charger, the processor can determine 520 whether a disconnection timer has expired (e.g., similar to the predetermined period of time before an alarm is initiated as discussed above in connection with FIG. 3). For example, as noted above, the alarm circuitry in the rechargeable battery can be configured to wait for period of time before outputting an alarm to provide the patient with time to replace the battery in the medical device controller or place on the charger. For example, a timer such as alarm timer 146 as described above can be configured to function as the disconnection timer. In certain examples, the disconnection timer period can include 30 seconds, one minute, two minutes, five minutes, and other similar periods of time. If the processor determines 520 that the disconnection timer has not expired, the processor can repeat the determination 510 if the rechargeable battery is attached to a medical device controller and/or the determination 515 whether the rechargeable battery is attached to a battery charger.

If the processor does determine 520 that the disconnection timer has elapsed, the processor can output 525 an alarm by, for example, providing a battery output status signal that indicates that the rechargeable battery is detached from both the wearable medical device controller and the battery charger to the alarm circuitry. The processor can then determine 530 whether the rechargeable battery has been properly attached to either the controller or the battery charger. If the processor determines 530 that the rechargeable battery has been attached, the processor can stop 535 the alarm by, for example, updating the battery output status signal to indicate that the rechargeable battery is attached.

Conversely, if the processor does not determine 530 that the battery is attached, the processor determines 540 if an alarm timer has elapsed. For example, the alarm circuitry can be configured to output the alarm for a certain period of time such as the predetermined alarm period as discussed above in connection with FIG. 3. After this period has elapsed, the alarm circuitry can be configured to automatically stop the alarm to, for example, preserve battery power. Similar to the disconnection timer as described above, a timer such as alarm timer 146 can be used as the alarm timer as described in FIG. 5. If the processor determines 540 that the alarm timer has not elapsed, the processor can maintain the battery output status signal and continue to output 525 the alarm. If the processor does determine 540 that the timer alarm has elapsed, the processor can update the battery output status signal to indicate that the alarm timer has elapsed and stop 535 the alarm.

It should be noted that the process 500 as shown in FIG. 5 is shown by way of example only. In actual implementation, the process 500 can include fewer or additional steps, various steps can be combined and/or reordered, and other similar adjustments to the process can be made. For example, in implementation, the monitoring 505 for battery attachment as well as the determining 510 whether the rechargeable battery is attached to the controller and the determining 515 whether the rechargeable battery is attached to the battery charger can be combined into a single monitoring and determinization step. Additionally, both determining 520 whether the disconnection timer has expired as well as determining 540 whether the alarm timer has expired are shown by way of example. In certain implementations, the processor can output 525 the alarm immediately upon determining that the rechargeable battery is not attached to either a medical device controller or a battery charger. Similarly, the processor can be configured to continue outputting the alarm until determining 530 that the rechargeable battery has been attached to a medical device controller or a battery charger without monitoring an alarm timer. Accordingly, the alarm timer expired step 540 can be an optional step, and the alarm can be configured to continue indefinitely or until the battery is attached to a controller and/or a charger.

In a use-case example, the above described processes and techniques can be implemented to reduce the risk of a patient wearing a wearable medical device, such as a WCD, but forgetting to replace a depleted rechargeable battery with a charged rechargeable battery during a battery swap. The above described processes and techniques can also reduce the risk that the patient will not properly insert the depleted rechargeable battery into the battery charger. For example, an elderly heart failure patient may be prescribed a WCD for continuous wear while also being given a battery charger and two rechargeable batteries. Upon the initial fitting of the wearable medical device, the patient can be instructed that the rechargeable batteries should be swapped every 24 hours and that, upon removal from the controller, the depleted rechargeable battery should be placed on the battery charger and left until the next battery swap. During the first battery swap, the patient may be confused or forget the instructions and fail to place the depleted rechargeable battery onto the battery charger. Using the techniques and processes as described herein, after a period of time (e.g., five minutes), the depleted rechargeable battery can begin to emit an audible and/or tactile alert reminding the patient that the depleted rechargeable battery should be placed on the battery charger. The alert(s) can continue until the patient places the rechargeable battery onto the battery charger. Without the alerts as taught herein, the patient might not remember to replace the depleted rechargeable battery onto the battery charger and, when the next battery swap occurs, the patient may not have a charged battery for insertion into the WCD, leaving the patient vulnerable to a potential cardiac event without a fully operating treatment device.

As noted above, in addition to including the detachment circuitry and alarm circuitry in the rechargeable battery, similar circuitry can be integrated into the battery charger as well. For example, FIG. 6 illustrates a battery charger 600 that is configured to recharge rechargeable batteries configured to provide power to, for example, a wearable medical device such as a WCD as described herein.

Figure 6:
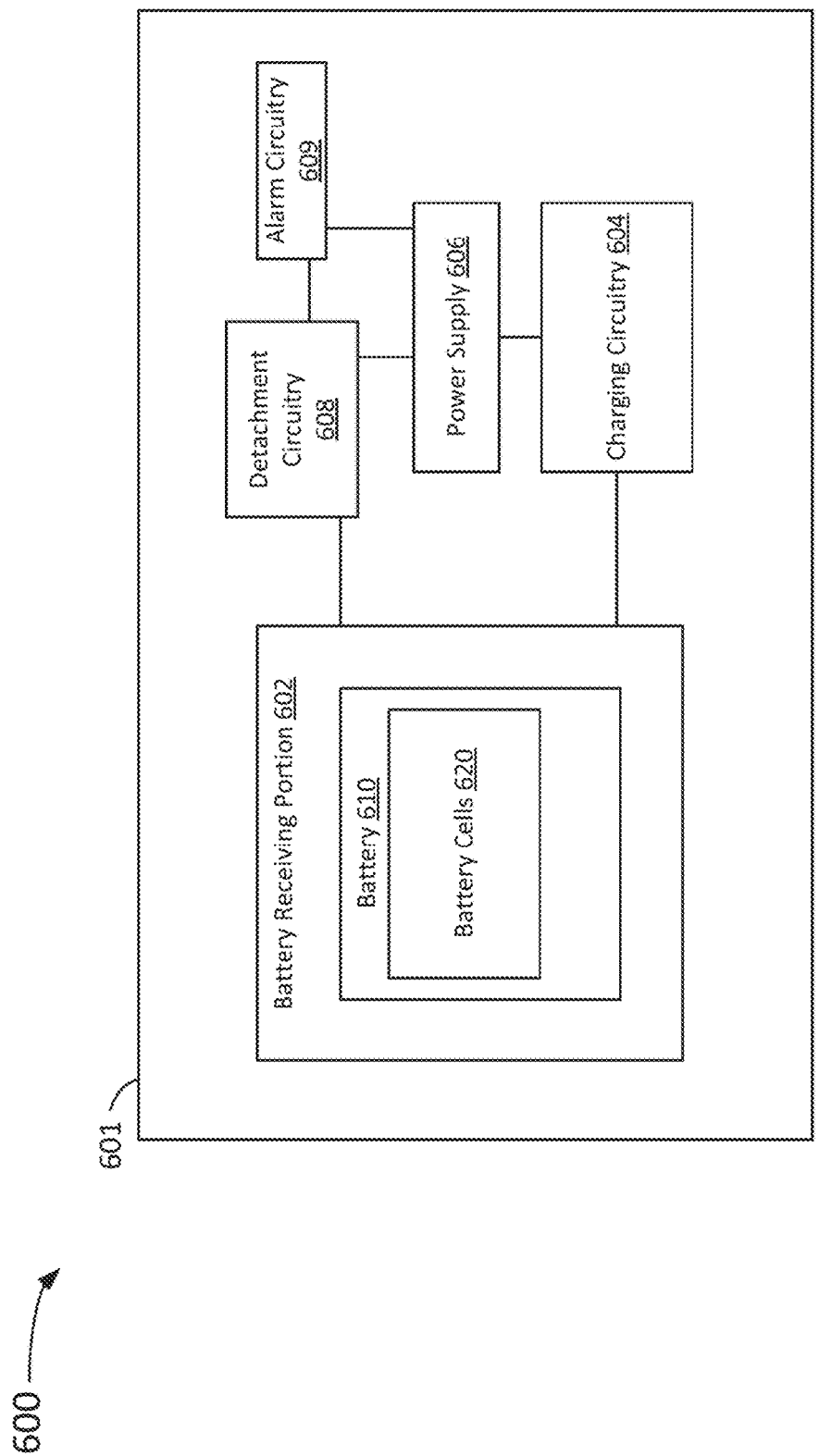
FIG. 6 illustrates a schematic view of a battery charger that includes detachment circuitry and alarm circuitry, in accordance with an example of the present disclosure.

As shown in FIG. 6, the battery charger 600 can include a housing 601 configured to house various components of the battery charger. For example, the housing 601 can be configured to include a battery receiving portion 602. The battery receiving portion 602 can include a recessed or similarly shaped cavity configured to physically receive at least a portion of the rechargeable battery 610. The battery receiving portion 602 can further include one or more electrical connectors configured to establish an electrical connection between the rechargeable battery 610 and charging circuitry 604. The charging circuitry 604 can include various electrical components arranged to condition power received from a power supply 606 into electrical signals suitable for charging the battery cells 620 of the rechargeable battery 610. For example, the power supply 606 can be a plug or other similar connector configured to plug into an electrical wall outlet and receive main power at, for example, 120 volts and 10 amps. The charging circuitry 604 can be configured to convert the main power to a level suitable for charging the rechargeable battery 610. For example, the charging circuitry 604 can be configured to convert the main power to about 5 volts at about 2.5 amps.

The battery charger 600 can also include detachment circuitry 608 and alarm circuitry 609. For example, the detachment circuitry 608 can be similar to detachment circuitry 132 as described above, as well as the examples of detachment circuitry shown in Table 1 and illustrated in FIGS. 4A-4F and described above. The alarm circuitry 609 can include similar components as alarm circuitry 134 as shown in FIG. 3 and described in detail above. In certain implementations, as the power supply 606 can be receiving power from a wall outlet, the alarm circuitry 609 can include additional output options such one or more recorded speech outputs stored on a memory in the alarm circuitry and configured to be output via a speaker or other similar output device as a patient alert. Similarly, the alarm circuitry 609 can include, for example, a text-to-speech translator configured to output one or more text alerts as speech outputs.

It should be noted that, as shown in FIG. 6, rechargeable battery 610 does not include detachment circuitry or alarm circuitry as described herein. However, it should be noted that this is shown by way of example only and, in certain implementations, a rechargeable battery such as rechargeable battery 110 that includes detachment circuitry 132 and alarm circuitry 134 can be used with battery charger 600, thereby providing for redundant alerts for a patient when the rechargeable battery is removed from the battery charger.

Figure 7A:
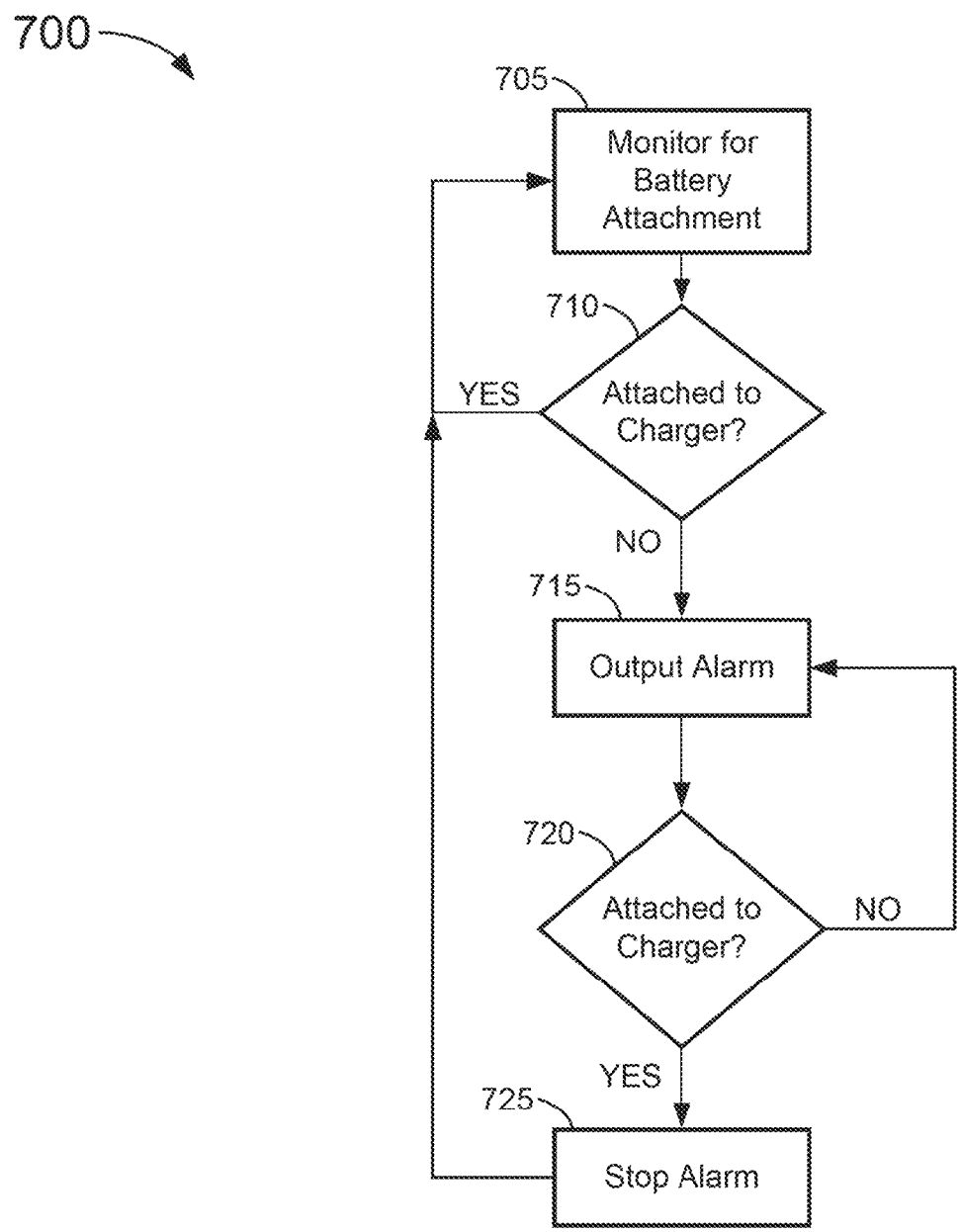
FIG. 7A illustrates an alternate process flow for monitoring battery attachment and providing an alarm if detached, in accordance with an example of the present disclosure.

FIG. 7A illustrates a sample process 700 for operating alarm circuitry when integrated into a battery charger as described above. In certain implementations, the detachment circuitry as described herein can include a processor or other similar computing device that is configured to perform a set of instructions to perform a process such as process 700 as described herein. For example, the processor can monitor 705 for battery attachment to the battery charger. For example, the battery charger can include one or more of the detachment circuit types as listed in Table 1 and described above. The output of the detachment circuit can be monitored 705 and, for example, the processor can determine 710 whether the rechargeable battery is properly attached to the battery charger. If the processor does determine 710 that the rechargeable battery is properly attached to the battery charger, the processor can continue to monitor 705 for battery attachment. If the processor does not determine 710 that the rechargeable battery is attached to the battery charger, the processor can output 715 an alarm by, for example, providing a battery output status signal that indicates that the rechargeable battery is detached from the battery charger to the alarm circuitry. The processor can then determine 720 whether the rechargeable battery has been properly attached to the battery charger. If the processor determines 720 that the rechargeable battery has been attached, the processor can stop 725 the alarm by, for example, updating the battery output status signal to indicate that the rechargeable battery is attached to the battery charger. If, conversely, the processor does not determine 720 that the rechargeable battery is attached, the processor can maintain the battery output status signal and continue to output 715 the alarm.

It should be noted that the process 700 as shown in FIG. 7A is shown by way of example only. In actual implementation, the process 700 can include fewer or additional steps, various steps can be combined and/or reordered, and other similar adjustments to the process can be made. For example, in implementation, the monitoring 705 for battery attachment as well as the determining 710 whether the rechargeable battery is attached to the battery charger can be combined into a single monitoring and determinization step. However, these are shown as separate steps in process 700 by way of example only. Similarly, process 700 as shown in FIG. 7A can include monitoring timing information such as a disconnection timer and an alarm timer as is described above in the discussion of FIG. 3 (e.g., the predetermined period of time and the predetermined alarm period as described in connection with FIG. 3) and in the discussion of process 500 as shown in FIG. 5.

Figure 7B:
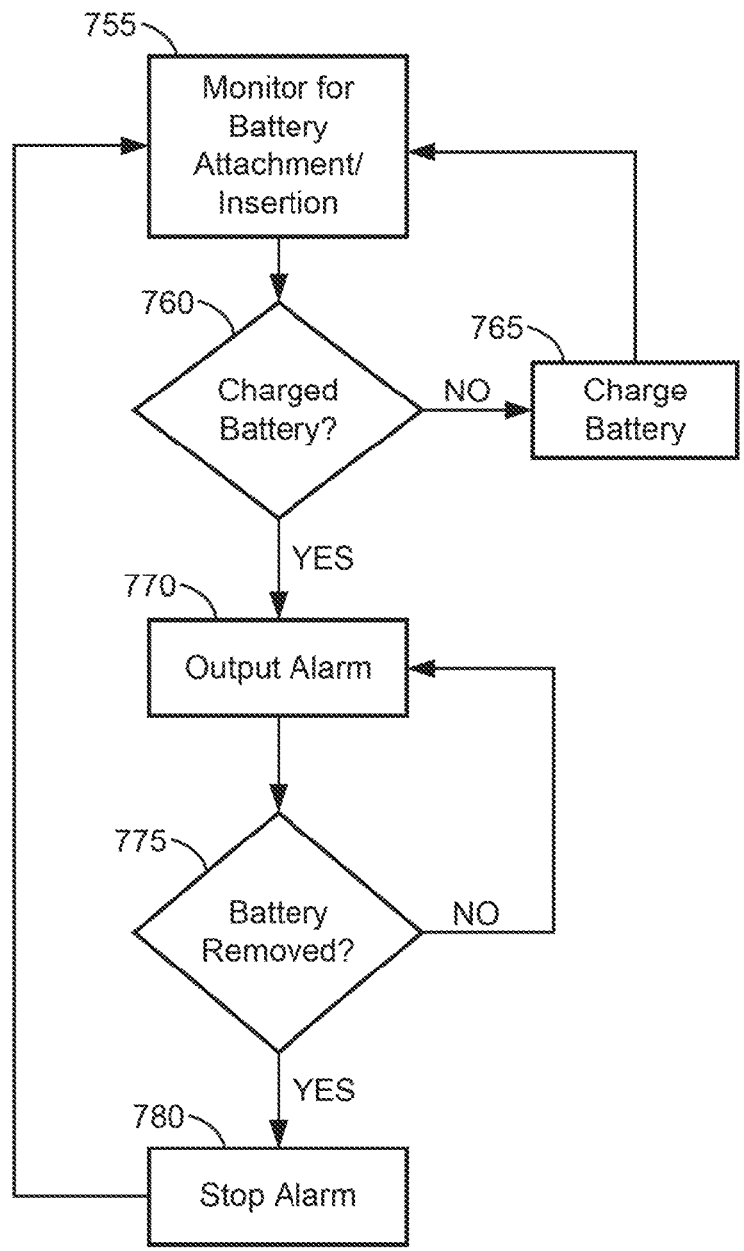
FIG. 7B illustrates a process for determining battery status for a rechargeable battery that has been placed on a battery charger, in accordance with an example of the present disclosure.

FIG. 7B illustrates a sample process 750 showing additional functionality that can be implemented in, for example, a battery charger as described herein. However, it should be noted that process 750 is shown as being implemented by the battery charger as an example only. In certain implementations, various process steps as included in process 750 can be performed by one or more processing components integrated into, for example, a rechargeable battery as described herein.

As shown in FIG. 7B, process 750 can include determining whether an appropriate rechargeable battery as been placed onto a battery charger for charging. For example, a patient might remove a rechargeable battery from the battery recharger to swap with a depleted battery and accidentally replace the charged rechargeable battery back onto the battery charger.

Referring to FIG. 7B, a processor, such as the processor as described above as implementing process 700, can monitor 755 for battery attachment/insertion of a rechargeable battery to the battery charger as described herein. If a rechargeable battery has been inserted or attached to the battery charger, the processor can determine 760 whether the rechargeable battery is already charged. If the processor determines 760 that the rechargeable battery is not charged, the battery charger can charge 765 the rechargeable battery. However, if the processor does determine 760 that the rechargeable battery has been charged, the processor can output 770 an alarm indicating that the rechargeable battery as newly placed into the battery charger is already charged. This alarm can provide an added indication to the patient that the rechargeable battery placed onto the charger may have been improperly placed.

As further shown in FIG. 7B, the processor can determine 775 if the rechargeable battery has been removed. If the rechargeable battery has been removed, the processor can stop 780 the alarm and monitor 755 for battery attachment or insertion. If the processor determines 775 that the rechargeable battery has not been removed, the processor can continue to output 770 the alarm.

It should be noted that the process 750 as shown in FIG. 7A is shown by way of example only. In actual implementation, the process 750 can include fewer or additional steps, various steps can be combined and/or reordered, and other similar adjustments to the process can be made. For example, in certain implementations, the patient may be able to provide confirmation that they acknowledge the rechargeable battery is already charged. Upon receiving such a confirmation, the processor can immediately stop 780 the alarm and return to monitoring 755 for battery attachment or insertion.

To continue the above use-case example, the patient may place a depleted rechargeable battery onto the battery charger during a battery swap. However, the patient might not confirm that the rechargeable battery is properly positioned and charging when placed on the charger. In such an example, the alarm circuitry in the battery charger as described above will provide an alert to the patient to check that the rechargeable battery is properly inserted into the battery charger. In another example, the patient may remove the rechargeable battery after a period of time such as twelve hours, having assumed that the time was adequate to fully charge the rechargeable battery. However, the instructions to the patient may include keeping the rechargeable battery in the battery charger until the rechargeable batteries are swapped. In such an example, the battery charger can provide an alert to the patient that there is currently no rechargeable battery in the battery charger, thereby prompting the patient to replace the rechargeable battery in the battery charger.

Figure 8:
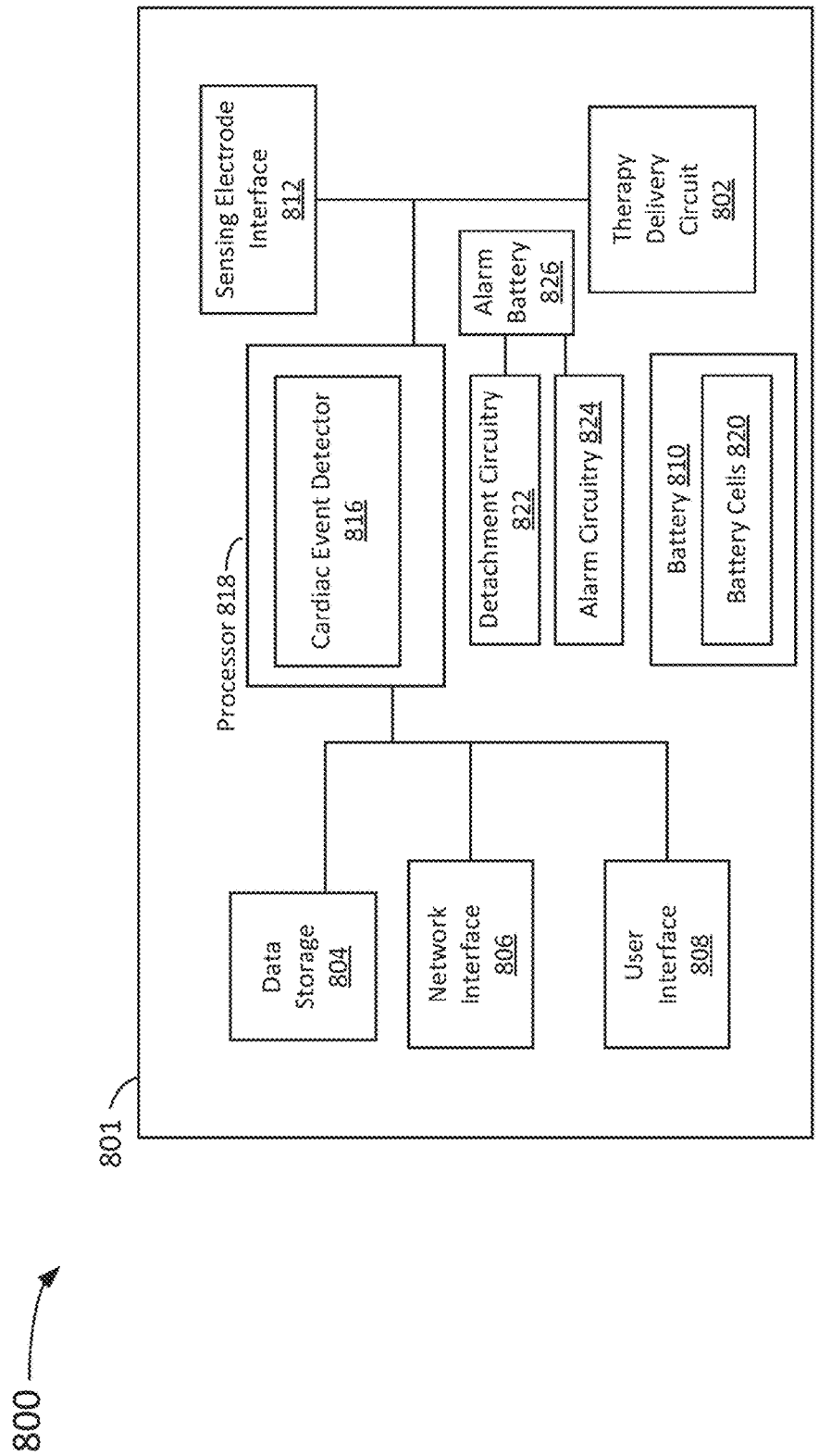
FIG. 8 illustrates a schematic view of a sample controller for a wearable medical device that includes detachment circuitry and alarm circuitry, in accordance with an example of the present disclosure.

As noted above, in addition to including the detachment circuitry and alarm circuitry in the rechargeable battery, similar circuitry can be integrated into the controller of a medical device as well. For example, FIG. 8 illustrates an example component-level view of the medical device controller 800 included in, for example, a wearable medical device such as a WCD. As shown in FIG. 8, the medical device controller 800 can include a housing 801 configured to house a therapy delivery circuitry 802, a data storage 804, a network interface 806, a user interface 808, at least one rechargeable battery 810, a sensor interface 812, a cardiac event detector 816, and least one processor 818. The medical device controller 800 can be configured to receive operational power from, for example, battery cells 820 as contained in rechargeable battery 810.

As further shown in FIG. 8, the medical device controller 800 can also include detachment circuitry 822 and alarm circuitry 824. For example, the detachment circuitry 822 can be similar to detachment circuitry 132 as described above, as well as the examples of detachment circuitry shown in Table 1 and illustrated in FIGS. 4A-4F and described above. The alarm circuitry 824 can include similar components as alarm circuitry 134 as shown in FIG. 3 and described in detail above. The medical device controller can also include an alarm battery 826 that is configured to provide power to the detachment circuitry 822 and/or the alarm circuitry 824. The alarm battery 826 can include, for example, a small removable battery such as a button battery configured to provide power to the detachment circuitry 822 and the alarm circuitry 824.

It should be noted that, as shown in FIG. 8, rechargeable battery 810 does not include detachment circuitry or alarm circuitry as described herein. However, it should be noted that this is shown by way of example only and, in certain implementations, a rechargeable battery such as rechargeable battery 110 that includes detachment circuitry 132 and alarm circuitry 134 can be used with controller 800, thereby providing for redundant alerts for a patient when the rechargeable battery is removed from the controller.

Figure 9A:
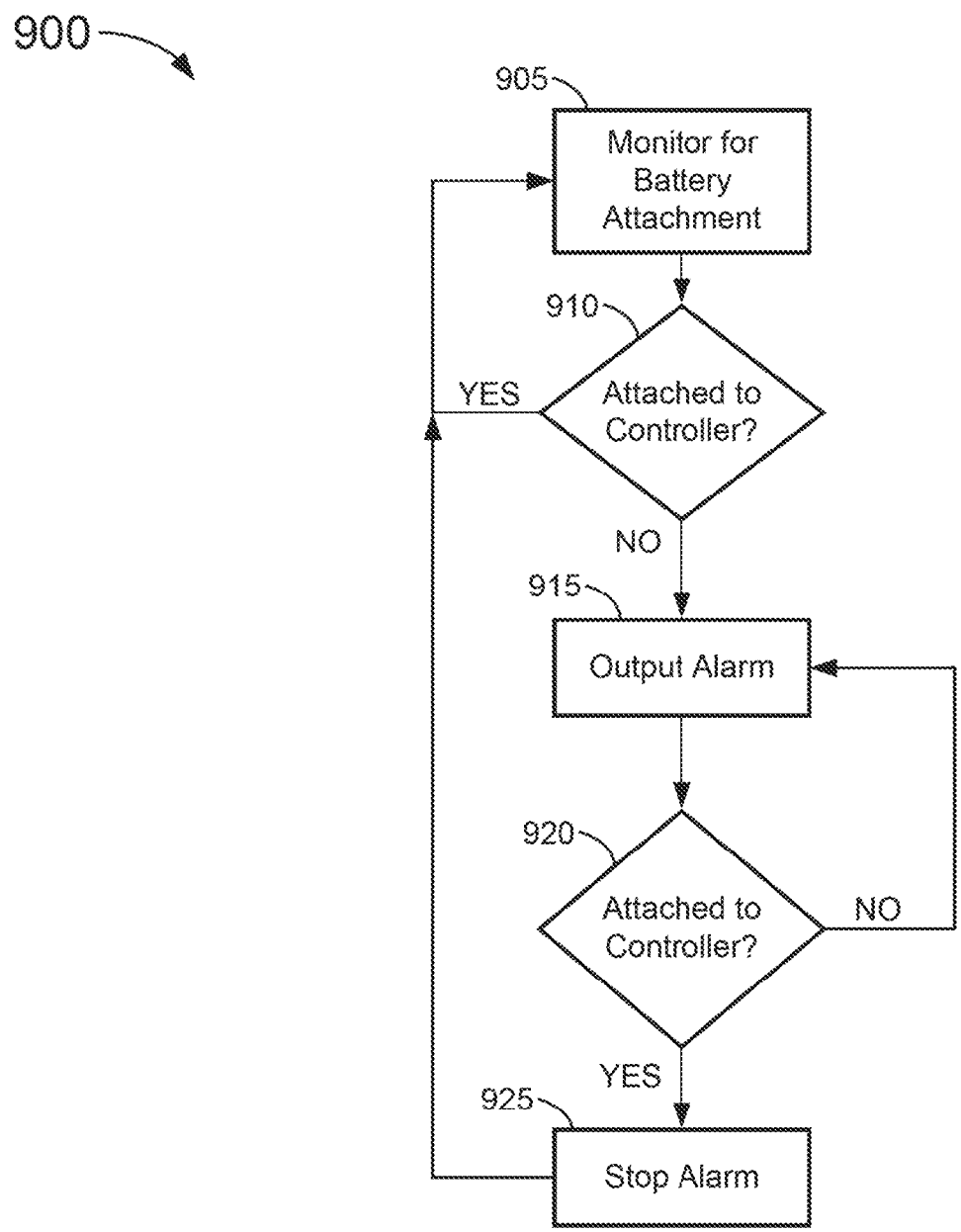
FIG. 9A illustrates an alternate process flow for monitoring battery attachment and providing an alarm if detached, in accordance with an example of the present disclosure.

FIG. 9A illustrates a sample process 900 for operating alarm circuitry when integrated into a controller of a wearable medical device as described above. In certain implementations, the detachment circuitry as described herein can include a processor or other similar computing device that is configured to perform a set of instructions to perform a process such as process 900 as described herein. For example, the processor can monitor 905 for battery attachment to the controller. For example, the controller can include one or more of the detachment circuit types as listed in Table 1 and described above. The output of the detachment circuit can be monitored 905 and, for example, the processor can determine 910 whether the rechargeable battery is properly attached to the controller and providing power to the controller. If the processor does determine 910 that the rechargeable battery is properly attached to the controller, the processor can continue to monitor 905 for battery attachment. If the processor does not determine 910 that the rechargeable battery is attached to the controller, the processor can output 915 an alarm by, for example, providing a battery output status signal that indicates that the rechargeable battery is detached from the controller to the alarm circuitry. The processor can then determine 920 whether the rechargeable battery has been properly attached to the controller. If the processor determines 920 that the rechargeable battery has been attached, the processor can stop 925 the alarm by, for example, updating the battery output status signal to indicate that the rechargeable battery is attached to the controller. If, conversely, the processor does not determine 920 that the rechargeable battery is attached, the processor can maintain the battery output status signal and continue to output 915 the alarm.

It should be noted that the process 900 as shown in FIG. 9A is shown by way of example only. In actual implementation, the process 900 can include fewer or additional steps, various steps can be combined and/or reordered, and other similar adjustments to the process can be made. For example, in implementation, the monitoring 905 for battery attachment as well as the determining 910 whether the rechargeable battery is attached to the controller can be combined into a single monitoring and determinization step. However, these are shown as separate steps in process 900 by way of example only. Similarly, process 900 as shown in FIG. 9A can include monitoring timing information such as a disconnection timer and an alarm timer as is described above in the discussion of FIG. 3 (e.g., the predetermined period of time and the predetermined alarm period as described in connection with FIG. 3) and in the discussion of process 500 as shown in FIG. 5.

Figure 9B:
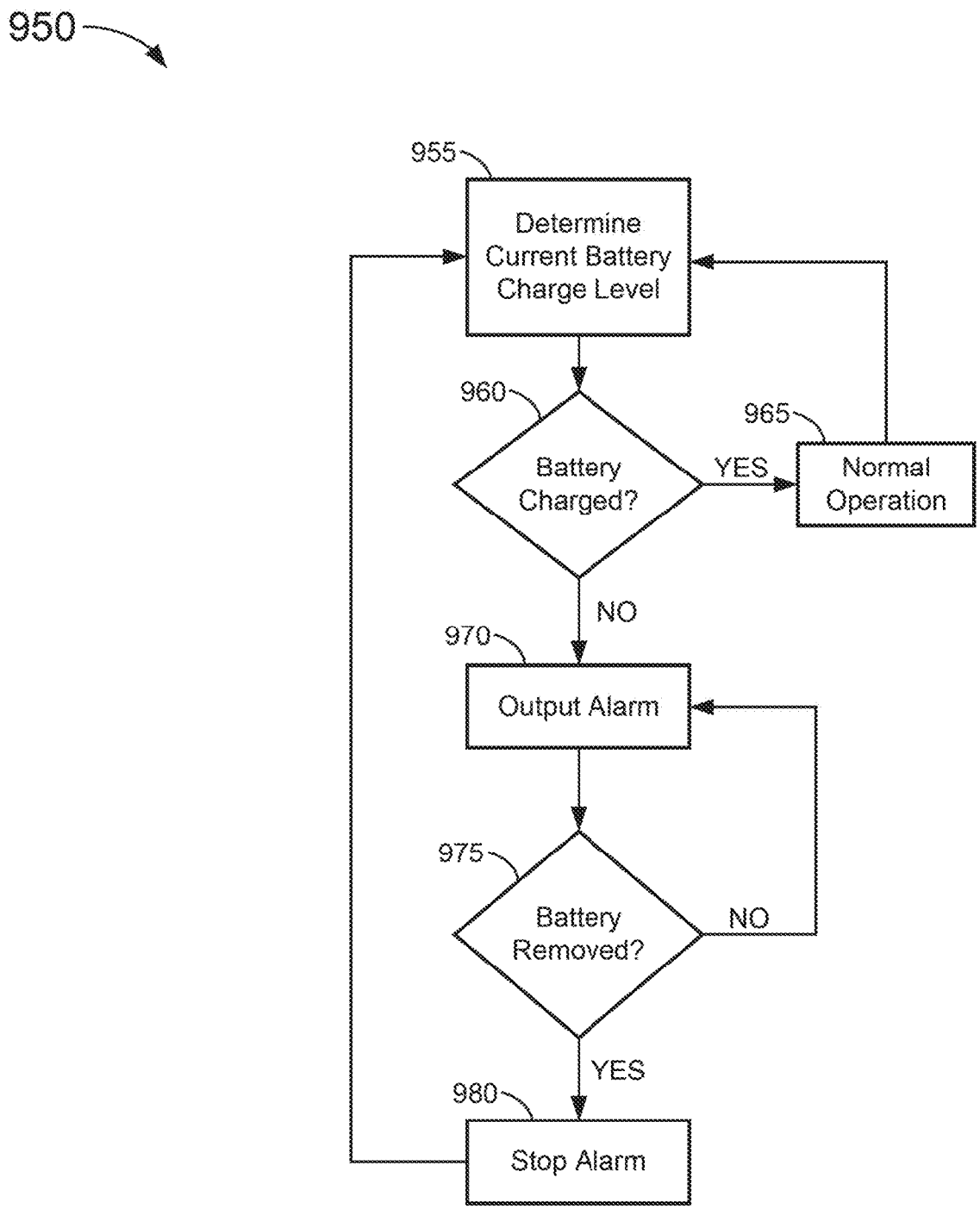
FIG. 9B illustrates a process for determining battery status for a rechargeable battery that has been inserted into a medical device controller, in accordance with an example of the present disclosure.

FIG. 9B illustrates a sample process 950 showing additional functionality that can be implemented in, for example, a medical device controller as described herein. However, it should be noted that process 950 is shown as being implemented by the controller as an example only. In certain implementations, various process steps as included in process 950 can be performed by one or more processing components integrated into, for example, a rechargeable battery as described herein.

As shown in FIG. 9B, process 950 can include determining a charge level for a rechargeable battery. For example, a patient might remove a depleted battery from the controller to swap with a charged rechargeable battery and accidentally replace the depleted rechargeable battery back into the controller. Similarly, a patient may simply forget to swap a depleted rechargeable battery in a timely manner.

Referring back to FIG. 9B, a processor (e.g., processor 118 as described herein) can determine 955 a current battery charge level for a rechargeable battery that is inserted into the controller. In order to provide normal operation, a rechargeable battery may need a certain percentage of its overall energy potential. For example, once a rechargeable battery drops below 40% of total potential energy, the rechargeable battery may be considered depleted and should be swapped as described herein. If the processor determines 960 that the currently inserted rechargeable battery is sufficiently charged (e.g., above 40%), the processor can continue 965 normal operation of the controller. Conversely, the if the processor determines 960 that the currently inserted rechargeable battery is not sufficiently charged, the processor can output 970 an alarm.

As further shown in FIG. 9B, the processor can determine 975 if the rechargeable battery has been removed. If the rechargeable battery has been removed, the processor can stop 980 the alarm and monitor for a new rechargeable battery attachment or insertion. Upon attachment/insertion of a new rechargeable battery, the process can determine 955 the current charge level of the rechargeable battery. If the processor determines 975 that the battery has not been removed, the processor can continue to output 970 the alarm.

It should be noted that the process 950 as shown in FIG. 9B is shown by way of example only. In actual implementation, the process 950 can include fewer or additional steps, various steps can be combined and/or reordered, and other similar adjustments to the process can be made. For example, in certain implementations, the patient may be able to snooze or otherwise temporarily silence (e.g., for five minutes) an alarm to provide time for the patient to swap a depleted rechargeable battery for a charged rechargeable battery. Upon receiving a snooze request from the patient, the processor can immediately stop 980 the alarm for a certain period of time (e.g., five minutes as noted above)

and, upon expiration of the period of time, determine 955 the current battery charge level as shown in FIG. 9B, thereby repeating at least a portion of process 950.

To continue the above use-case example, the patient may forget to insert a charged rechargeable battery into a controller of a wearable medical device such as a WCD during a battery swap. However, the patient might immediately leave their house or the area of their house where they keep their batteries and may not hear an alert being issued by the battery. In such an example, the alarm circuitry in the medical device controller as described above will provide an alert to the patient to check that the rechargeable battery is properly inserted into the medical device controller, thus reducing or eliminating the risk that a patient may be wearing a medical device that does not have a rechargeable battery inserted and providing the device power.

Figure 10A:
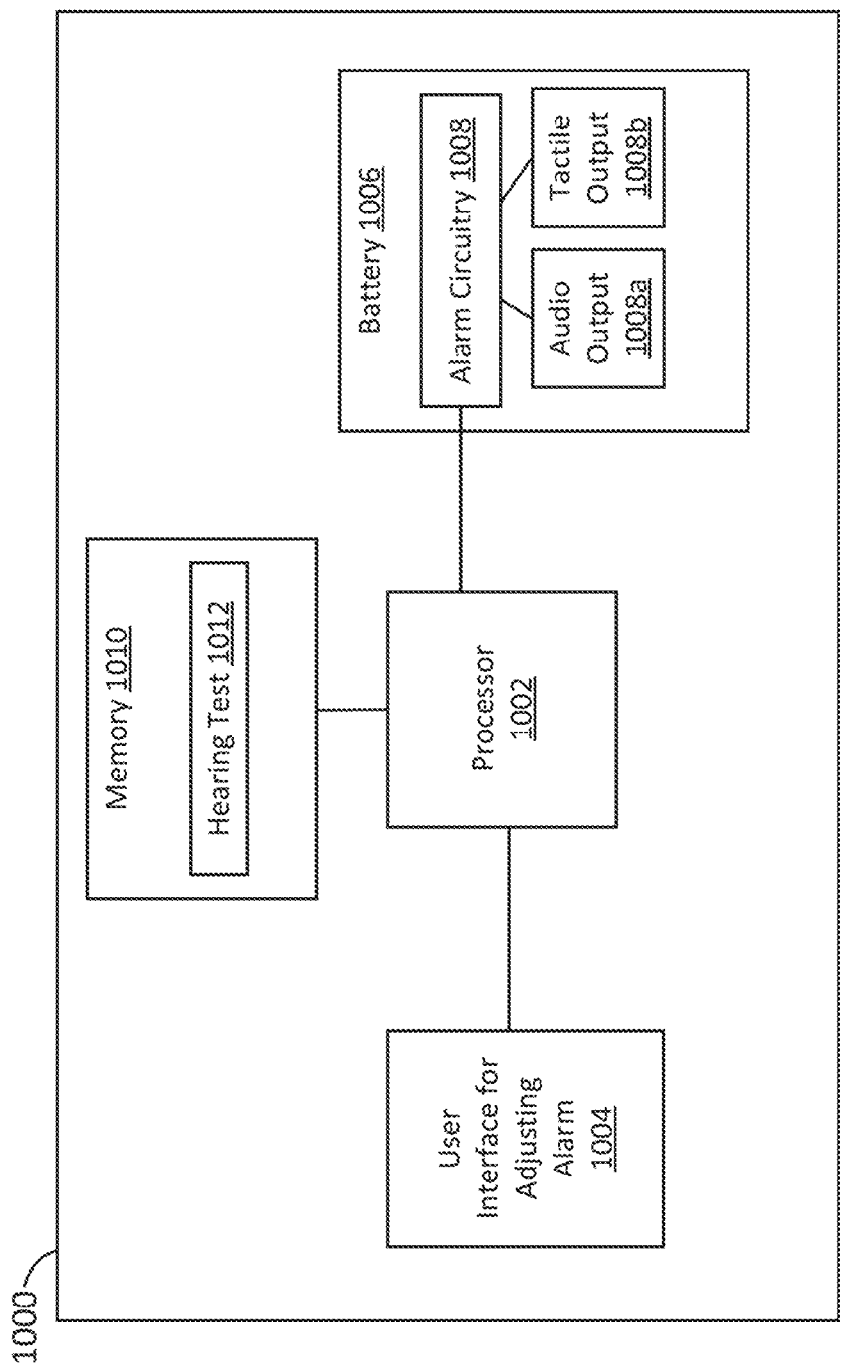
FIG. 10A illustrates a schematic view of a controller including an interface for adjusting an alarm, in accordance with an example of the present disclosure.

In certain examples, a patient may have one or more physical conditions that require a specialized or custom alert. For example, a patient may be deaf or only able to hear sounds broadcast at specific tones or frequencies. In order to provide a custom alert, a healthcare provider or other similar caretaker can use one or more customization options included, for example, into a controller for a wearable medical device. FIG. 10A illustrates a sample component-level view of a portion of a wearable medical device controller 1000 that includes various options for customizing an alert targeted for a specific patient. As shown in FIG. 10A, the controller 1000 can include a processor 1002 operably connected to a user interface 1004. The user interface 1004 can be configured to provide an interactive user interface screen for adjusting one or more parameters of the alarm circuitry, thereby adjusting the output alerts. For example, these one or more parameters can be stored in a memory operably coupled to or integrated into alarm circuitry 1008 or, in certain implementations, in memory 1010 as shown in FIG. 10 and described below.

In addition, the controller 1000 can include a rechargeable battery 1006 including, in this example, alarm circuitry 1008 as well as audio output 1008*a* and tactile output 1008*b*. Based upon a user's interaction with the user interface 1004, various parameters such as volume, duration, tone, frequency, and other similar alert parameters can be adjusted for the alarm circuitry 1008 and/or the audio output 1008*a* and tactile output 1008*b*.

As further shown in FIG. 10A, the controller 1000 can include a memory 1010 operably coupled to the processor 1002 and configured to store, in addition to various instructions executed by the processor during normal operation of the controller, instructions for initiating and performing a hearing test 1012. For example, the hearing test 1012 can be performed during an initial fitting of a patient for a wearable medical device and can determine a current hearing condition of the patient. For example, the hearing test can include outputting a number of different audio tones at different frequencies. The person administering the initial fitting, or the patient, can interact with the user interface 1004 to provide an indication of whether the patient heard an individual tone or not. Based upon this information, the processor 1002 can determine what tones the patient is most likely to hear and adjust the parameters of the alarm circuitry 1008 to output an audio alert including one or more of the determined tones. In certain implementations, the parameters can include one or more spoken alerts that can be played for the patient and, based upon patient response, can be selected to be output as the audio alert. When outputting an alert, the alarm circuitry 1008 can then access the alert parameters and output an appropriate alert customized or otherwise selected for a particular patient.

It should be noted that the alarm circuitry 1008 is shown as being integrated into rechargeable battery 1006 by way of example only in FIG. 10A. In certain implementations, the alarm circuitry 1008 (and audio output 1008*a* and tactile output 1008*b*) can be integrated into the controller 1000 or both the controller and the rechargeable battery 1006.

Figure 10B:
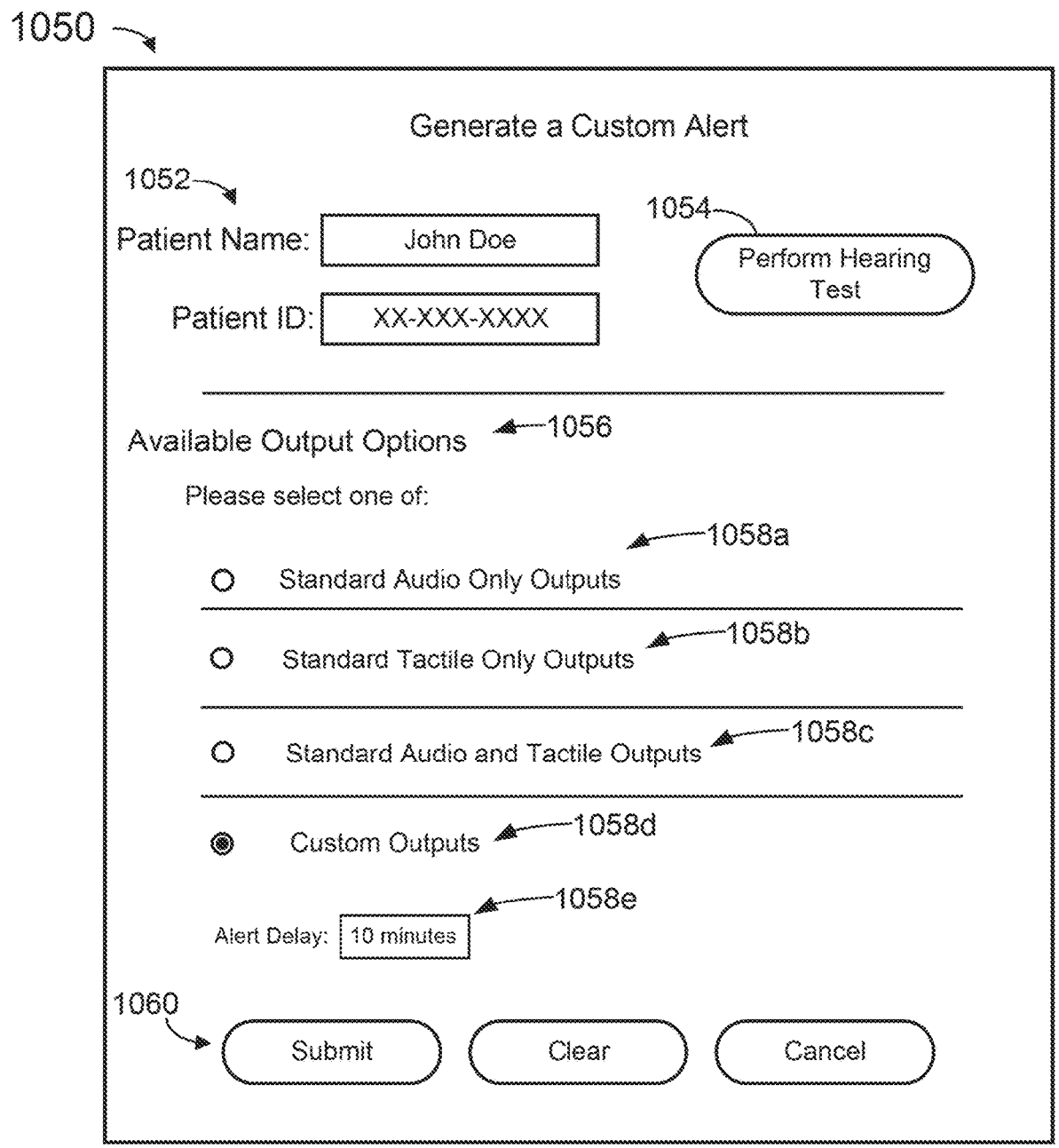
FIG. 10B illustrates a view of a sample user interface that a physician or other healthcare provider can access to generate or modify alerts for a patient, in accordance with an example of the present disclosure.

FIG. 10B illustrates one example of a user interface screen 1050 that the processor 1002 is configured to provide according to some examples. More specifically, FIG. 10B illustrates a sample view of a user interface screen 1050 that can be accessed and utilized by a physician and/or other healthcare provider or patient caretaker to adjust one or more alarm parameters as described above. For example, the user interface screen 1050 can be implemented and displayed on a portion of the user interface 1004 as shown in FIG. 10A.

As illustrated in FIG. 10B, the user interface screen 1050 includes user interface controls 1052, 1054, 1056, and 1060. In some examples, the user interface control 1052 provides access to patient specific information such as the cardiac patient's name and an identifier associated with the cardiac patient. This information can be entered by a person performing the initial patient fitting or can be entered when the device is initially prescribed to the patient by, for example, a physician. In certain implementations, the user interface control 1054 can include a button or other selectable control. In some examples, the processor 1002 responds to input selecting the user interface control 1054 by automatically initiating the hearing test 1012 as shown in FIG. 10A and described above.

Additionally, as further shown in FIG. 10B, the user interface screen can include user interface control 1056. The user interface control 1056 can include selectable plan controls 1058*a*, 1058*b*, 1058*c*, 1058*d*, and 1058*e*, each of which can be related to altering one or more alarm parameters. For example, selectable plan controls 1058*a*, 1058*b*, 1058*c*, and 1058*d* can include a radio selection button that allows a user interacting with user interface screen 1050 to select from a preset type of alert (1058*a*, 1058*b*, 1058*c*) or to select a custom output (1058*d*). Additionally, the selectable plan control 1058*e* can provide the user with a fillable form that allows the user to set an alert delay. For example, the alert delay can represent the amount of time between battery removal/detachment and when the first alert is issued. For example, the selectable control 1058*e* can include a user-provided numerical value for the alert delay entered in minutes. For example, as shown in FIG. 10B, the alert delay has been set to ten minutes. However, this is provided by way of example only and additional delay times can be included. For example, the alert delay can be set to one minute, two minutes, five minutes, ten minutes, 15 minutes, 30 minutes, 60 minutes, and 120 minutes.

It should be noted that selectable control 1058*e* is shown as a fillable form by way of example only. In certain implementations, selectable control 1058*e* can be implemented as another type of selectable control such as a drop-down menu.

As further shown in FIG. 10B, the user interface control 1060 includes a set of selectable buttons. In response to receiving a selection of the "submit" button, the processor can adjust one or more of the alarm parameters as described herein. In response to receiving a selection of the "clear" button, the processor can delete existing selections and/or entered information from the user interface screen 1050. In response to receiving a section of the "cancel" button, the processor can abort alert customization.

In certain implementations, it may be advantageous or desirable to provide a tool or mechanism to turn off or further delay an alarm. For example, when returning a wearable medical device after having worn it for the prescribed time, the patient may want to turn off any alerts issued by the rechargeable batteries, medical device controller, and/or battery charger. For example, the battery charger can include a switch or other mechanical interface that turns off the alert. Similarly, the medical device controller can include a switch or other similar mechanical interface for turning off the alert. In some examples, the medical device controller can include an access to remove the alarm battery as described above. The battery can be removed for regular replacement or to stop an alert when the device is not being used.

Figure 11:
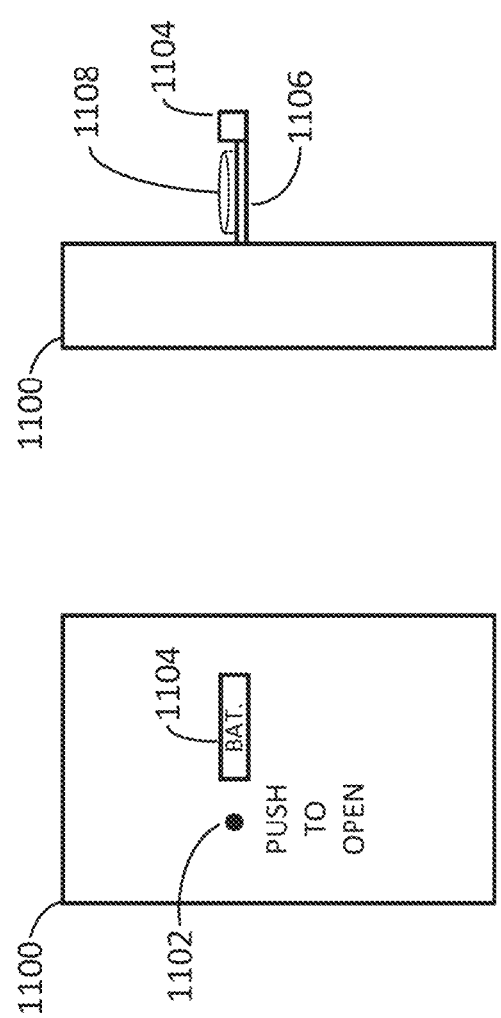
FIG. 11 illustrates a view of a battery removal mechanism for a controller of a wearable medical device, in accordance with an example of the present disclosure.

For example, FIG. 11 illustrates an example mechanical interface for removing an alarm battery such as a button battery as described above. The left image in FIG. 11 shows a front view of a portion of a medical device controller 1100, and the right image of FIG. 11 shows a side view of the portion of the controller. As shown in the front view, the controller 1100 can include a button 1102 or other similar release mechanism. For example, the button 1102 can include a hole that a patient or other authorized user can insert a small object such as a paperclip to release a battery compartment 1104. In certain implementations, button 1102 can include a hole that requires a specially-shaped key or other similar unique release tool to prevent tampering or unauthorized access to the battery compartment 1104.

As shown in the side view of FIG. 11, the battery compartment can include a small drawer 1106 into which a button battery 1108 is placed. Upon release, the battery 1108 can be removed or replaced, and the battery compartment 1104 can be closed.

Figure 12:
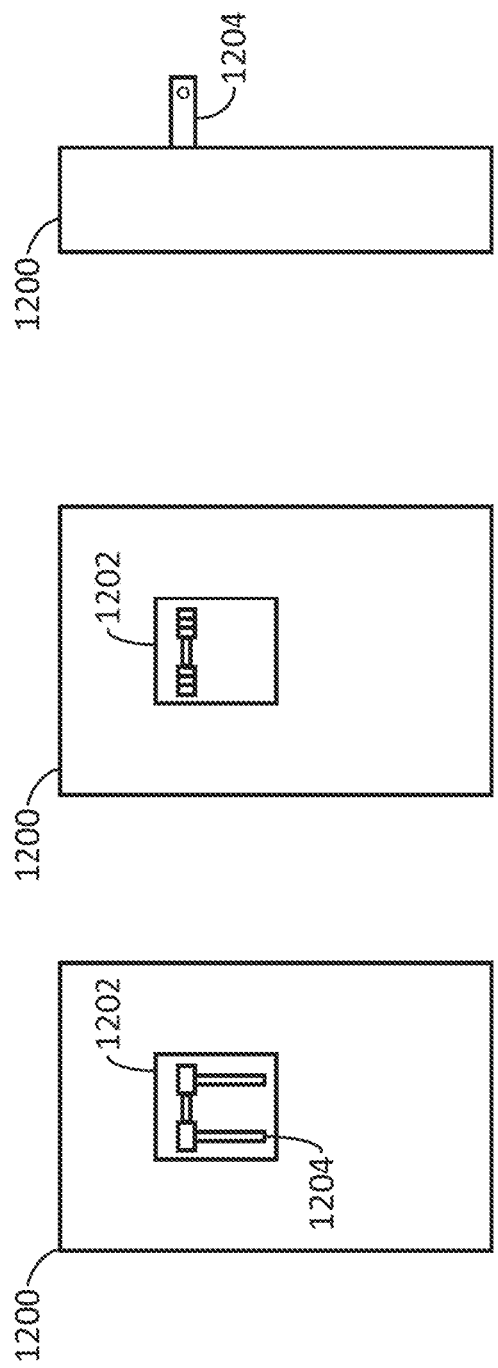
FIG. 12 illustrates a view of a folding plug integrated into a portion of a rechargeable battery, in accordance with an example of the present disclosure.

Similarly, one or more mechanisms can be included on a rechargeable battery for stopping, muting, or otherwise snoozing (e.g., delaying) an alert. For example, FIG. 12 illustrates a battery 1200 that includes a folding or otherwise retractable plug 1204. When folded, the plug 1204 is contained within a recess 1202 in the battery 1200 so as to not disrupt the overall exterior form factor of the battery. Once unfolded or otherwise extended, the plug 1204 can be inserted into, for example, a wall output or other similar power source. When plugged into a power source, the battery 1200 can delay or otherwise stop any alerts being issued by the battery. For example, internal power regulation circuitry (e.g., power regulation circuitry 140 as described above) can be configured to determine when a power supply is providing power to the plug 1204. Upon detecting power at the plug 1204, the power regulation circuitry can stop or otherwise delay an alert.

It should be noted that the examples as shown in FIGS. 11 and 12 are provided by way of example only and other mechanisms can be used to delay or stop an alert. For example, unplugging the battery charger can stop an alert being issued by the battery charger. Similarly, the controller can include a user-accessible menu where the patient can access various features. In this menu, the patient can select to disable an alert upon completion of the prescribed usage of the wearable medical device.

The teachings of the present disclosure can be generally applied to external medical monitoring and/or treatment devices that are powered by a battery. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 1 illustrates an example component-level view of a medical device controller 100 included in, for example, a wearable medical device. As further shown in FIG. 1, the therapy delivery circuitry 102 can be coupled to one or more electrodes 120 configured to provide therapy to the patient. For example, the therapy delivery circuitry 102 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 118) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 102 can be configured to perform the switching and pulse delivery operations, e.g., under control of the processor 118. As the energy is delivered to the patient, the amount of energy being delivered can be tracked. For example, the amount of energy can be kept to a predetermined constant value even as the pulse waveform is dynamically controlled based on factors such as the patient's body impedance while the pulse is being delivered.

In certain examples, the therapy delivery circuitry 102 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 104 can include one or more of non-transitory computer-readable media, such as flash memory, solid state memory, magnetic memory, optical memory, cache memory, combinations thereof, and others. The data storage 104 can be configured to store executable instructions and data used for operation of the medical device controller 100. In certain examples, the data storage can include executable instructions that, when executed, are configured to cause the processor 118 to perform one or more operations. In some examples, the data storage 104 can be configured to store information such as ECG data as received from, for example, the sensing electrode interface.

In some examples, the network interface 106 can facilitate the communication of information between the medical device controller 100 and one or more other devices or entities over a communications network. For example, where the medical device controller 100 is included in an ambulatory medical device, the network interface 106 can be configured to communicate with a remote computing device such as a remote server or other similar computing device. The network interface 106 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 100. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 108 can include one or more physical interface devices such as input devices, output devices, and combination input/output devices and a software stack configured to drive operation of the devices. These user interface elements can render visual, audio, and/or tactile content. Thus, the user interface 108 can receive input or provide output, thereby enabling a user to interact with the medical device controller 100.

The medical device controller 100 can also include at least one rechargeable battery 110 configured to provide power to one or more components integrated in the medical device controller 100. The rechargeable battery 110 can include a rechargeable multi-cell battery pack. In one example implementation, the rechargeable battery 110 can include three or more 2200 mAh lithium ion cells that provide electrical power to the other device components within the medical device controller 100. For example, the rechargeable battery 110 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 100.

The sensor interface 112 can include physiological signal circuitry that is coupled to one or more sensors configured to monitor one or more physiological parameters of the patient. As shown, the sensors can be coupled to the medical device controller 100 via a wired or wireless connection. The sensors can include one or more ECG sensing electrodes 122, and non-ECG physiological sensors 123 such as vibration sensor 124, tissue fluid monitors 126 (e.g., based on ultra-wide band radiofrequency devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 122 can be configured to monitor a patient's ECG information. For example, by design, the digital sensing electrodes 122 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 122 can be used with an electrolytic gel dispersed between the electrode surface and the patient's skin. In certain implementations, the electrodes 122 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 1, the vibration sensors 124 be configured to detect cardiac or pulmonary vibration information. For example, the vibration sensors 124 can detect a patient's heart valve vibration information. For example, the vibration sensors 124 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 124 can also be configured to detect heart wall motion, for instance, by placement of the sensor in the region of the apical beat. The vibration sensors 124 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 124 can also include a multi-channel accelerometer, for example, a three-channel accelerometer configured to sense movement in each of three orthogonal axes such that patient movement/body position can be detected and correlated to detected cardio-vibrations information. The vibration sensors 124 can transmit information descriptive of the cardio-vibrations information to the sensor interface 112 for subsequent analysis.

The tissue fluid monitors 126 can use radio frequency (RF) based techniques to assess fluid levels and accumulation in a patient's body tissue. For example, the tissue fluid monitors 126 can be configured to measure fluid content in the lungs, typically for diagnosis and follow-up of pulmonary edema or lung congestion in heart failure patients. The tissue fluid monitors 126 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 126 can transmit information descriptive of the tissue fluid levels to the sensor interface 112 for subsequent analysis.

In certain implementations, the cardiac event detector 116 can be configured to monitor a patient's ECG signal for an occurrence of a cardiac event such as an arrhythmia or other similar cardiac event. The cardiac event detector can be configured to operate in concert with the processor 118 to execute one or more methods that process received ECG signals from, for example, the sensing electrodes 122 and determine the likelihood that a patient is experiencing a cardiac event. The cardiac event detector 116 can be implemented using hardware or a combination of hardware and software. For instance, in some examples, cardiac event detector 116 can be implemented as a software component that is stored within the data storage 104 and executed by the processor 118. In this example, the instructions included in the cardiac event detector 116 can cause the processor 118 to perform one or more methods for analyzing a received ECG signal to determine whether an adverse cardiac event is occurring. In other examples, the cardiac event detector 116 can be an application-specific integrated circuit (ASIC) that is coupled to the processor 118 and configured to monitor ECG signals for adverse cardiac event occurrences. Thus, examples of the cardiac event detector 116 are not limited to a particular hardware or software implementation.

In some implementations, the processor 118 includes one or more processors (or one or more processor cores) that each are configured to perform a series of instructions that result in manipulated data and/or control the operation of the other components of the medical device controller 100. In some implementations, when executing a specific process (e.g., cardiac monitoring), the processor 118 can be configured to make specific logic-based determinations based on input data received and be further configured to provide one or more outputs that can be used to control or otherwise inform subsequent processing to be carried out by the processor 118 and/or other processors or circuitry with which processor 118 is communicatively coupled. Thus, the processor 118 reacts to specific input stimulus in a specific way and generates a corresponding output based on that input stimulus. In some example cases, the processor 118 can proceed through a sequence of logical transitions in which various internal register states and/or other bit cell states internal or external to the processor 118 can be set to logic high or logic low. As referred to herein, the processor 118 can be configured to execute a function where software is stored in a data store coupled to the processor 118, the software being configured to cause the processor 118 to proceed through a sequence of various logic decisions that result in the function being executed. The various components that are described herein as being executable by the processor 118 can be implemented in various forms of specialized hardware, software, or a combination thereof. For example, the processor 118 can be a digital signal processor (DSP) such as a 24-bit DSP. The processor 118 can be a multi-core processor, e.g., having two or more processing cores. The processor 118 can be an Advanced RISC Machine (ARM) processor such as a 32-bit ARM processor or a 64-bit ARM processor. The processor 118 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 118 of the controller 100 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 13A:
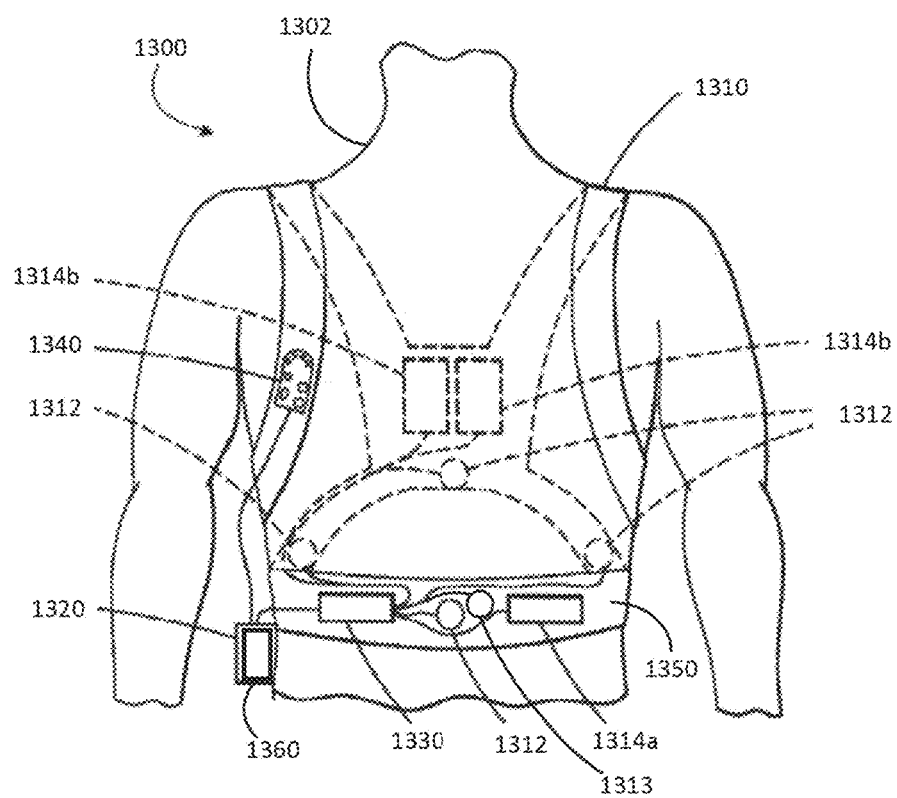
FIGS. 13A-13D depict sample ambulatory medical devices that may be prescribed to a heart failure patient, in accordance with an example of the present disclosure.

FIG. 13A illustrates an example medical device 1300 that is external, ambulatory, and wearable by a patient 1302, and configured to implement one or more configurations described herein. For example, the medical device 1300 can be a non-invasive medical device configured to be located substantially external to the patient. Such a medical device 1300 can be, for example, an ambulatory medical device that is capable of and designed for moving with the patient as the patient goes about his or her daily routine. For example, the medical device 1300 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1300 can include one or more of the following: a garment 1310, one or more ECG sensing electrodes 1312, one or more non-ECG physiological sensors 1313, one or more therapy electrodes 1314a and 1314b (collectively referred to herein as therapy electrodes 1314), a medical device controller 1320 (e.g., controller 100 as described above in the discussion of FIG. 1), a connection pod 1330, a patient interface pod 1340, a belt 1350, or any combination of these. In some examples, at least some of the components of the medical device 1300 can be configured to be affixed to the garment 1310 (or in some examples, permanently integrated into the garment 1310), which can be worn about the patient's torso.

The medical device controller 1320 can be operatively coupled to the sensing electrodes 1312, which can be affixed to the garment 1310, e.g., assembled into the garment 1310 or removably attached to the garment, e.g., using hook and loop fasteners. In some implementations, the sensing electrodes 1312 can be permanently integrated into the garment 1310. The medical device controller 1320 can be operatively coupled to the therapy electrodes 1314. For example, the therapy electrodes 1314 can also be assembled into the garment 1310, or, in some implementations, the therapy electrodes 1314 can be permanently integrated into the garment 1310. In an example, the medical device controller 1320 includes a patient user interface 1360 to allow a patient interface with the externally-worn device. For example, the patient can use the patient user interface 1360 to respond to pre- and post-workout questions, prompts, and surveys as described herein.

Component configurations other than those shown in FIG. 13A are possible. For example, the sensing electrodes 1312 can be configured to be attached at various positions about the body of the patient 1302. The sensing electrodes 1312 can be operatively coupled to the medical device controller 1320 through the connection pod 1330. In some implementations, the sensing electrodes 1312 can be adhesively attached to the patient 1302. In some implementations, the sensing electrodes 1312 and at least one of the therapy electrodes 1314 can be included on a single integrated patch and adhesively applied to the patient's body.

The sensing electrodes 1312 can be configured to detect one or more cardiac signals. Examples of such signals include ECG signals and/or other sensed cardiac physiological signals from the patient. In certain examples, as described herein, the non-ECG physiological sensors 1313 are sensors such as accelerometers, vibrational sensors, and other measuring devices for recording additional non-ECG physiological parameters. For example, as described above, the non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1314 can also be configured to include sensors configured to detect ECG signals as well as other physiological signals of the patient. The connection pod 1330 can, in some examples, include a signal processor configured to amplify, filter, and digitize these cardiac signals prior to transmitting the cardiac signals to the medical device controller 1320. One or more of the therapy electrodes 1314 can be configured to deliver one or more therapeutic defibrillating shocks to the body of the patient 1302 when the medical device 1300 determines that such treatment is warranted based on the signals detected by the sensing electrodes 1312 and processed by the medical device controller 1320. Example therapy electrodes 1314 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1314 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 13B:
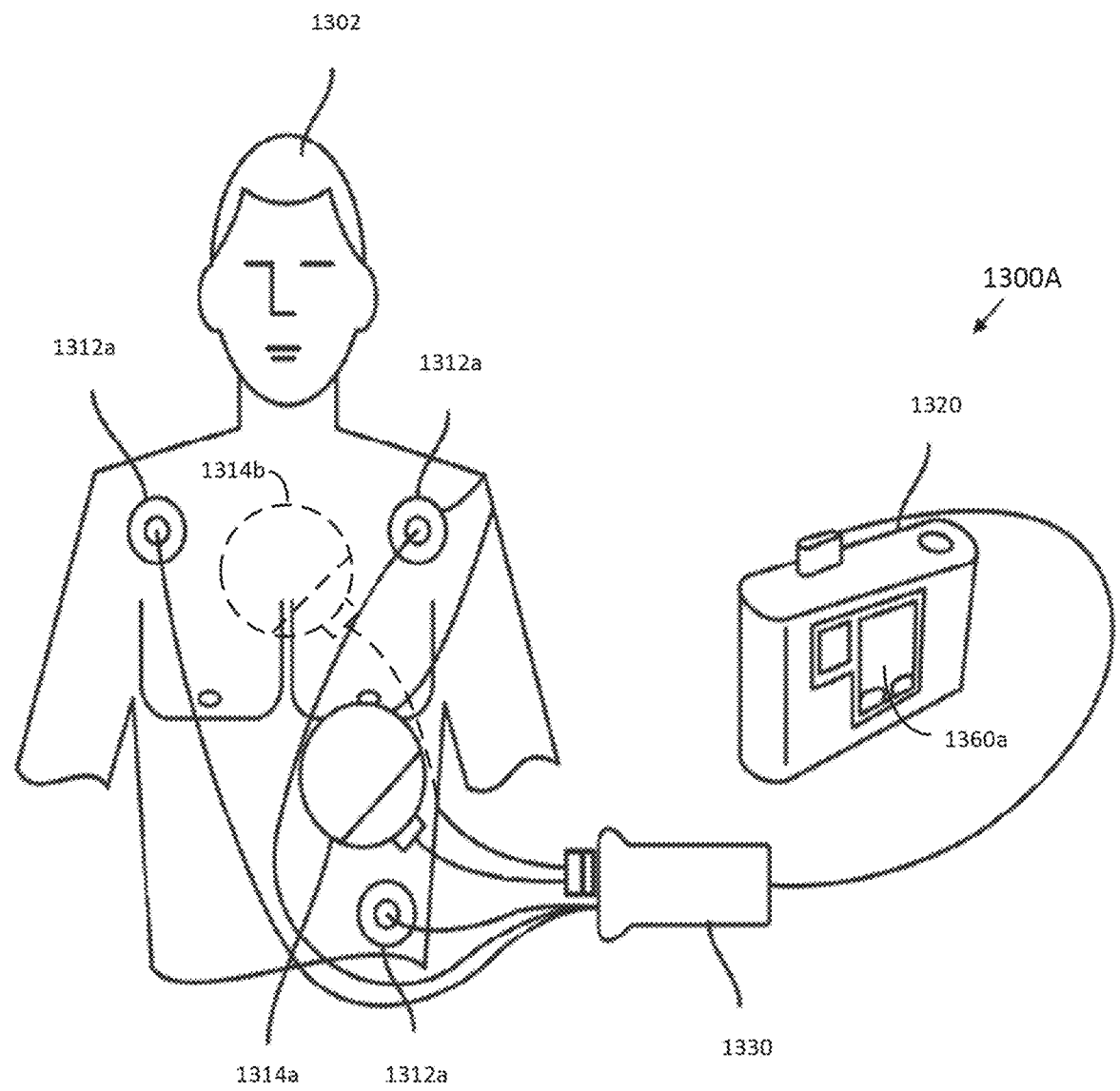

FIG. 13B illustrates a hospital wearable defibrillator 1300A that is external, ambulatory, and wearable by a patient 1302. Hospital wearable defibrillator 1300A can be configured in some implementations to provide pacing therapy, e.g., to treat bradycardia, tachycardia, and asystole conditions. The hospital wearable defibrillator 1300A can include one or more ECG sensing electrodes 1312a, one or more therapy electrodes 1314a and 1314b, a medical device controller 1320 and a connection pod 1330. For example, each of these components can be structured and function as like number components of the medical device 1300. For example, the electrodes 1312a, 1314a, 1314b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1314a attaches to the front of the patient's torso to deliver pacing or defibrillating therapy. Similarly, the back adhesively attachable therapy electrode 1314b attaches to the back of the patient's torso. In an example scenario, at least three ECG adhesively attachable sensing electrodes 1312a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1360a can be configured to interact with a user other than the patient, e.g., a nurse, for device-related functions such as initial device baselining, setting and adjusting patient parameters, and changing the device batteries.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 13A.

Figure 13C:
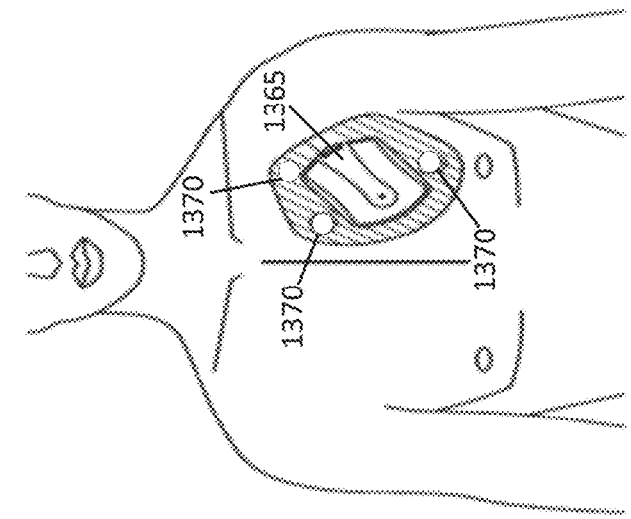
Figure 13C:
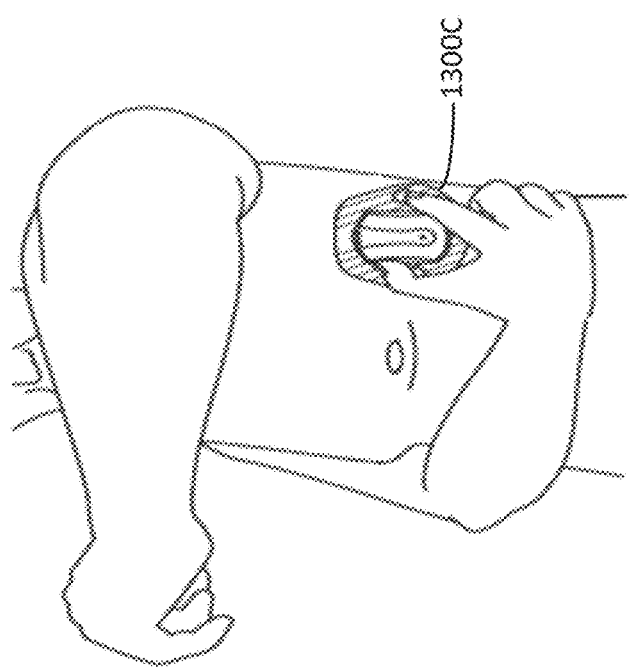
Figure 13D:
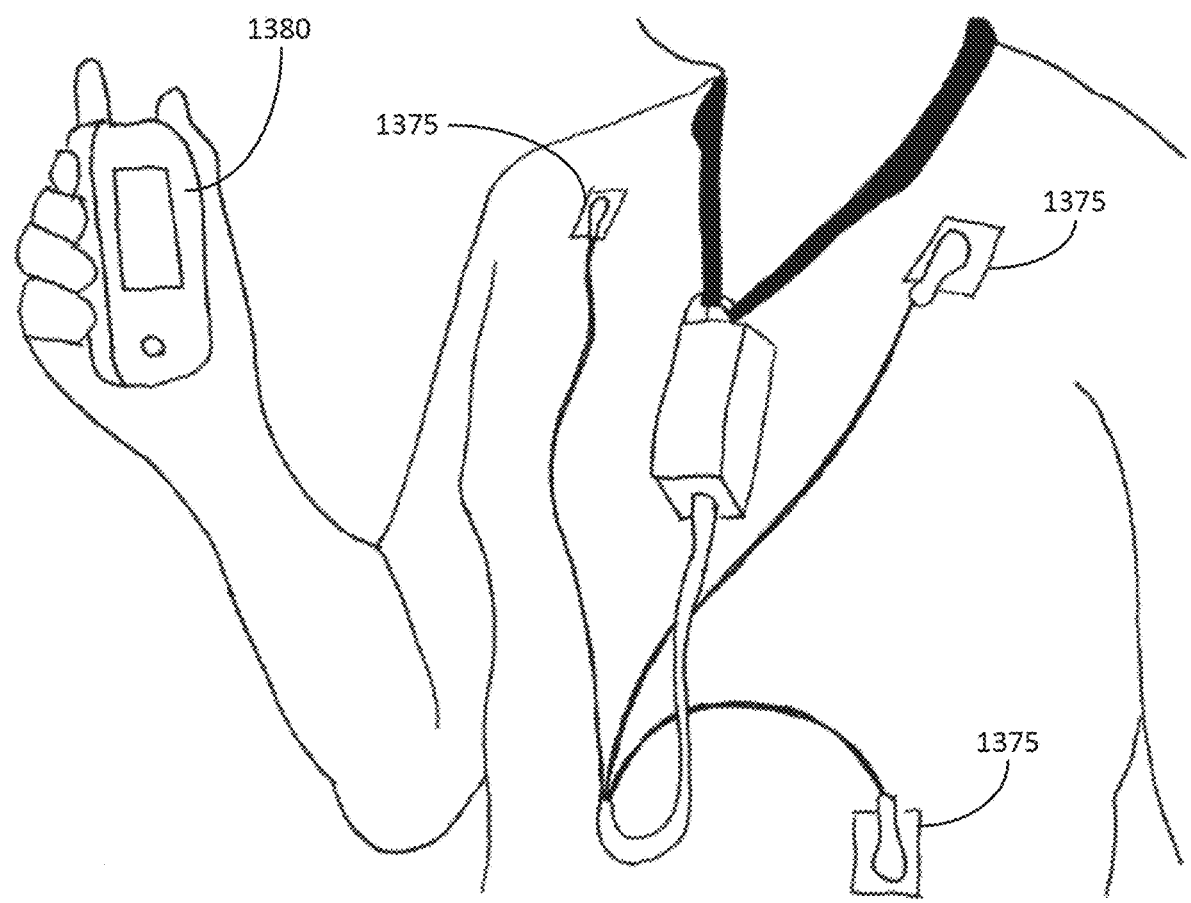

FIGS. 13C and 13D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 13C, an example wearable patient monitoring device 1300C can include tissue fluid monitors 1365 that use radio frequency (RF) based techniques to assess fluid levels and accumulation in a patient's body tissue. Such tissue fluid monitors 1365 can be configured to measure fluid content in the lungs, typically for diagnosis and follow-up of pulmonary edema or lung congestion in heart failure patients. The tissue fluid monitors 1365 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1300C may be a cardiac monitoring device that also includes digital sensing electrodes 1370 for sensing ECG activity of the patient. Device 1300C can pre-process the ECG signals via one or more ECG processing and/or conditioning circuits such as an ADC, operational amplifiers, digital filters, signal amplifiers under control of a microprocessor. Device 1300C can transmit information descriptive of the ECG activity and/or tissue fluid levels via a network interface to a remote server for analysis.

Referring to FIG. 13D, another example wearable cardiac monitoring device can be attached to a patient via at least three adhesive digital cardiac sensing electrodes 1375 disposed about the patient's torso. The cardiac devices illustrated in FIGS. 13C and 13D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring device for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 13A-D) can communicate with a remote server via an intermediary device 1380 such as that shown in FIG. 13D. For instance, devices such as shown in FIGS. 13A-D can be configured to include a network interface communications capability as described herein in reference to, for example, FIG. 1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An externally worn cardiac monitoring and treatment system with battery detachment detection, the system comprising:
    a battery-powered externally worn cardiac device comprising
        a therapy electrode configured to deliver a therapeutic shock to a patient wearing the battery-powered externally worn cardiac device,
        a housing, and
        at least one processor disposed in the housing and being configured to process one or more ECG signals of the patient wearing the battery-powered externally worn cardiac device and determine at least one arrhythmia based on the one or more ECG signals, wherein the at least one arrhythmia is one or more of ventricular fibrillation, ventricular tachycardia, bradycardia, tachycardia, or asystole; and
    a rechargeable battery detachably disposed within the housing of the battery-powered externally worn cardiac device and removably coupled to the at least one processor, the rechargeable battery comprising
        at least one battery cell,
        detachment circuitry configured to
            detect whether the rechargeable battery is detached from the battery-powered externally worn cardiac device by monitoring a connection established between the rechargeable battery and the at least one processor, and
            output a battery status signal indicating that the rechargeable battery is detached from the battery-powered externally worn cardiac device, thereby rendering the system unable to deliver the therapeutic shock, and
        at least one of audible or vibrational alarm circuitry operably coupled to the detachment circuitry, the at least one audible or vibrational alarm circuitry configured to
            receive the battery status signal, and
            output at least one of an audible alert in a predetermined frequency range or a tactile alert if the rechargeable battery is detached.

2. The system of claim 1, wherein the detachment circuitry is further configured to:
    determine whether the rechargeable battery is inserted into a battery charger by monitoring for a recharging current going from the battery charger to the at least one battery cell; and
    output an updated battery status signal indicating whether the rechargeable battery is inserted into the battery charger.

3. The system of claim 2, wherein the at least one audible or vibrational alarm circuitry is further configured to:
    determine whether the rechargeable battery is inserted into the battery charger based upon the updated battery status signal; and
    stop the output of the at least one audible alert in the predetermined frequency range or the tactile alert if the rechargeable battery is inserted into the battery charger.

4. The system of claim 1, wherein the at least one audible or vibrational alarm circuitry comprises at least one output device that is adjustable to alter the predetermined frequency range of the audible alert.

5. The system of claim 1, wherein the detachment circuitry comprises a detachment processor configured to:
    detect whether the rechargeable battery is detached from the battery-powered externally worn cardiac device; and
    output the battery status signal.

6. The system of claim 1, wherein the battery-powered externally worn cardiac device further comprises a plurality of sensing electrodes configured to be coupled externally to the patient and to detect the one or more ECG signals of the patient wearing the battery-powered externally worn cardiac device.

7. The system of claim 1, wherein the rechargeable battery is configured to provide power to the therapy electrode to deliver the therapeutic shock to the patient wearing the battery-powered externally worn cardiac device.

8. The system of claim 1, wherein the at least one audible or vibrational alarm circuitry is further configured to output the at least one audible alert in the predetermined frequency range or the tactile alert after a period of time has elapsed after the rechargeable battery is detached, the period of time comprising at least one of one minute, two minutes, five minutes, ten minutes, fifteen minutes, twenty minutes, thirty minutes, one hour, or two hours.

9. The system of claim 1, wherein the detachment circuitry comprises:
digital monitoring circuitry configured to monitor at least one data connection between the rechargeable battery and the at least one processor when the rechargeable battery is connected to the battery-powered externally worn cardiac device; and
at least one of
analog monitoring circuitry configured to monitor for one or more of a voltage drop in the at least one battery cell or a current flow from the at least one battery cell; or
at least one proximity detector configured to measure whether the rechargeable battery is attached to the battery-powered externally worn cardiac device.

10. A battery-powered externally worn cardiac device with battery detachment detection, the device comprising:
a plurality of sensing electrodes configured to be coupled externally to a patient and to detect one or more ECG signals of the patient wearing the battery-powered externally worn cardiac device;
a therapy electrode configured to deliver a therapeutic shock to the patient wearing the battery-powered externally worn cardiac device;
a housing;
at least one processor disposed in the housing and being configured to process the one or more ECG signals of the patient wearing the battery-powered externally worn cardiac device and determine at least one arrhythmia based on the one or more ECG signals, wherein the at least one arrhythmia is one or more of ventricular fibrillation, ventricular tachycardia, bradycardia, tachycardia, or asystole;
a rechargeable battery removably coupled to the at least one processor; and
a battery detection circuit comprising
at least one battery cell,
detachment circuitry configured to:
determine whether the rechargeable battery is attached to the battery-powered externally worn cardiac device, and
output a battery status signal indicating that the rechargeable battery is detached from the battery-powered externally worn cardiac device, thereby rendering the battery-powered externally worn cardiac device unable to deliver the therapeutic shock, and
at least one of audible or vibrational alarm circuitry operably coupled to the detachment circuitry, the at least one of audible or vibrational alarm circuitry configured to
receive the battery status signal, and
output at least one of an audible alert in a predetermined frequency range or a tactile alert if the rechargeable battery is detached.

11. The device of claim 10, wherein the detachment circuitry comprises:
digital monitoring circuitry configured to monitor at least one data connection between the rechargeable battery and the at least one processor when the rechargeable battery is attached to the battery-powered externally worn cardiac device; and at least one of
analog monitoring circuitry configured to monitor for one or more of a voltage drop in the at least one battery cell or a current flow from the at least one battery cell; or
at least one proximity detector configured to measure whether the rechargeable battery is attached to the battery-powered externally worn cardiac device.

12. The device of claim 10, wherein the at least one audible or vibrational alarm circuitry comprises at least one audio output device that is adjustable to alter the predetermined frequency range of the audible alert.

13. The device of claim 10, wherein the at least one battery cell is configured to provide power to one or more of the detachment circuitry or the at least one audible or vibrational alarm circuitry.

14. The device of claim 13, wherein the housing comprises a user-accessible battery compartment configured to:
house the at least one battery cell; and
provide access to the at least one battery cell for removal of the at least one battery cell to disconnect power to one or more of the detachment circuitry or the at least one audible or vibrational alarm circuitry.

15. The device of claim 10, wherein the rechargeable battery is configured to provide power to the therapy electrode to deliver the therapeutic shock to the patient wearing the battery-powered externally worn cardiac device.

* * * * *

UNITED STATES PATENT AND TRADEMARK OFFICE
CERTIFICATE OF CORRECTION

| | | |
|---|---|---|
| PATENT NO. | : 11,890,102 B2 | Page 1 of 1 |
| APPLICATION NO. | : 17/060398 | |
| DATED | : February 6, 2024 | |
| INVENTOR(S) | : James A. Patterson, III, Nathan J. Berry Ann and Sean M. Nickel | |

It is certified that error appears in the above-identified patent and that said Letters Patent is hereby corrected as shown below:

In the Specification

Column 22, Line 2 - delete "as been", insert -- has been --

Signed and Sealed this
Twenty-eighth Day of May, 2024

Katherine Kelly Vidal
*Director of the United States Patent and Trademark Office*